United States Patent
Sibley et al.

(10) Patent No.: US 12,145,922 B2
(45) Date of Patent: Nov. 19, 2024

(54) SELECTIVE D3 DOPAMINE RECEPTOR AGONISTS AND METHODS OF THEIR USE

(71) Applicants: The United States of America, as represented by the Secretary, Department of Health and Human Services, Bethesda, MD (US); The University of Kansas, Lawrence, KS (US); The University of North Carolina at Chapel Hill, Chapel Hill, NC (US)

(72) Inventors: David R. Sibley, Bethesda, MD (US); Amy Elizabeth Moritz, Bethesda, MD (US); R. Benjamin Free, Bethesda, MD (US); Joseph P. Steiner, Bethesda, MD (US); Noel Terrence Southall, Rockville, MD (US); Marc Ferrer, Rockville, MD (US); Xin Hu, Rockville, MD (US); Warren S. Weiner, Boston, MA (US); Jeffrey Aubé, Chapel Hill, NC (US); Kevin Frankowski, Chapel Hill, NC (US)

(73) Assignees: The United States of America, as represented by the Secretary, Department of Health and Human Services, Bethesda, MD (US); The University of Kansas, Lawrence, KS (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 18/111,241

(22) Filed: Feb. 17, 2023

(65) Prior Publication Data
US 2023/0312511 A1 Oct. 5, 2023

Related U.S. Application Data

(63) Continuation of application No. 16/093,365, filed as application No. PCT/US2017/027618 on Apr. 14, 2017, now Pat. No. 11,634,404.
(Continued)

(51) Int. Cl.
*C07D 401/12* (2006.01)
*A61P 25/28* (2006.01)
(Continued)

(52) U.S. Cl.
CPC ............ *C07D 401/12* (2013.01); *A61P 25/28* (2018.01); *C07D 209/42* (2013.01);
(Continued)

(58) Field of Classification Search
CPC ..... A61P 25/28; C07D 401/12; C07D 209/42; C07D 213/65; C07D 213/81; C07D 235/24; C07D 295/185; C07D 307/85; C07D 317/64; C07D 333/70; C07D 405/12; C07D 409/12; C07D 471/04
See application file for complete search history.

(56) References Cited

U.S. PATENT DOCUMENTS 5,932,734 A 8/1999 Yuan et al.
6,444,674 B1 9/2002 Hellendahl et al.
(Continued)

FOREIGN PATENT DOCUMENTS

CN 102285962 A 12/2011
EP 1484330 A1 12/2004
(Continued)

OTHER PUBLICATIONS

Shi et al., Neurosci Bull, Feb. 1, 2011, 27(1): 36-44.*
Database Registry [online], Chemical Abstracts ServicE, Aug. 3, 2012, XP002773048, retrieved from STN Database accession No. 1386162-69-1, abstract.
Database Registry [online], Chemical Abstracts Service; Apr. 17, 2007, XP002773055, retrieved from STN Database accession No. 930440-50-9, abstract.
(Continued)

*Primary Examiner* — Alicia L Otton
(74) *Attorney, Agent, or Firm* — CANTOR COLBURN LLP

(57) ABSTRACT

The disclosure of a compound of Formula I or a pharmaceutically acceptable salt thereof

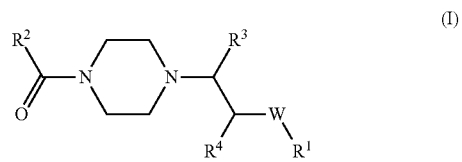

The variables W, $R^1$, $R^2$, $R^3$, and $R^4$ are defined in the disclosure. The disclosure provides a compound or salt of Formula I together with a pharmaceutically acceptable carrier. The disclosure also provides methods of treating a patient for Parkinson's disease and related syndromes, dyskinesia, especially dyskinesias secondary to treating Parkinson's disease with L-DOPA, neurodegenerative disorders such as Alzheimer's disease and dementia, Huntington's disease, restless legs syndrome, bipolar disorder and depression, schizophrenia, cognitive dysfunction, or substance use disorders, the methods comprising administering a compound of Formula I or salt thereof to the patient. The disclosure provides combination methods of treatment in which the compound of Formula I is administered to the patient together with one or more additional active agents.

21 Claims, 10 Drawing Sheets

Related U.S. Application Data

(60) Provisional application No. 62/322,361, filed on Apr. 14, 2016.

(51) Int. Cl.
| | |
|---|---|
| *C07D 209/42* | (2006.01) |
| *C07D 213/65* | (2006.01) |
| *C07D 213/81* | (2006.01) |
| *C07D 235/24* | (2006.01) |
| *C07D 295/185* | (2006.01) |
| *C07D 307/85* | (2006.01) |
| *C07D 317/64* | (2006.01) |
| *C07D 333/70* | (2006.01) |
| *C07D 405/12* | (2006.01) |
| *C07D 409/12* | (2006.01) |
| *C07D 471/04* | (2006.01) |

(52) U.S. Cl.
CPC ......... *C07D 213/65* (2013.01); *C07D 213/81* (2013.01); *C07D 235/24* (2013.01); *C07D 295/185* (2013.01); *C07D 307/85* (2013.01); *C07D 317/64* (2013.01); *C07D 333/70* (2013.01); *C07D 405/12* (2013.01); *C07D 409/12* (2013.01); *C07D 471/04* (2013.01)

(56) References Cited

U.S. PATENT DOCUMENTS

| | | |
|---|---|---|
| 2009/0054449 A1 | 2/2009 | Geneste et al. |
| 2021/0323941 A1 | 10/2021 | Sibley et al. |

FOREIGN PATENT DOCUMENTS

| | | |
|---|---|---|
| WO | 03002543 A1 | 1/2003 |
| WO | 2008016973 A1 | 2/2008 |
| WO | 2010123995 A1 | 10/2010 |
| WO | 2017181004 A1 | 10/2017 |

OTHER PUBLICATIONS

Database Registry [online], Chemical Abstracts Service; Apr. 19, 2007, XP002773054, retrieved from STN Database accession No. 930893-33-7, abstract.
Database Registry [online], Chemical Abstracts Service; Apr. 25, 2008, XP002773056, retrieved from STN Database accession No. 1017214-96-8, abstract.
Database Registry [online], Chemical Abstracts Service; Aug. 15, 2011, XP002773050, retrieved from STN Database accession No. 1318173-92-0, abstract.
Database Registry [online], Chemical Abstracts Service; Aug. 16, 2011, XP002773049, retrieved from STN Database accession No. 1318530-74-3, abstract.
Database Registry [online], Chemical Abstracts Service; Jan. 29, 2009, XP002773051, retrieved from STN Database accession No. 1097612-59-3, abstract.
Database Registry [online], Chemical Abstracts Service; Jan. 29, 2009, XP002773052, retrieved from STN Database accession No. 1097492-13-1, abstract.
Database Registry [online], Chemical Abstracts Service; May 20, 2009, XP002773047, retrieved from STN Database accession No. 1147661-57-1, abstract.
Database Registry [online], Chemical Abstracts Service; May 24, 2011, XP002773053, retrieved from STN Database accession No. 1299403-53-4, abstract.
Guo et al., "Discovery of 1-aryloxyethyl piperazine derivatives as Kv1.5 potassium channel inhibitors (part I)," European Journal of Medicinal Chemistry; 2014, pp. 89-94, vol. 81.
International Preliminary Report on Patentability; International Application No. PCT/US2017/027618; International Filing Date—Apr. 14, 2017; Date of Issuance—Oct. 16, 2018; 10 pages.
International Search Report; International Application No. PCT/US2017/027618; International Filing Date: Apr. 14, 2017; Date of Mailing: Sep. 7, 2017; 10 pages.
Kanojia et al., "Synthesis and Class III Type Antiarrhythmic Activity of 4-Aroyl (and Aryl)-1-aralkylpiperazines," Bioorganic & Medicinal Chemistry Letters; 2000, pp. 2819-2823, vol. 10.
STN Registry database entry for CAS RN 1097 492-13-1, Entered STN Jan. 29, 2009, Accessed Jan. 14, 2022.
Written Opinion; International Application No. PCT/US2017/027618; International Filing Date: Apr. 14, 2017; Date of Mailing: Sep. 7, 2017; 11 pages.

\* cited by examiner

|   | A | B | C | D | E | F |
|---|---|---|---|---|---|---|
| 1 | 5-HT1A | 5-HT5A | Alpha2C | D4 | H4 | NET |
| 2 | 5-HT1B | 5-HT6 | Beta1 | D5 | KOR | PBR |
| 3 | 5-HT1D | 5-HT7 | Beta2 | DAT | M1 | SERT |
| 4 | 5-HT1E | Alpha1A | Beta3 | DOR | M2 | Sigma 1 |
| 5 | 5-HT2A | Alpha1B | BZP Site | GABAA | M3 | Sigma 2 |
| 6 | 5-HT2B | Alpha1D | D1 | H1 | M4 | |
| 7 | 5-HT2C | Alpha2A | D2 | H2 | M5 | |
| 8 | 5-HT3 | Alpha2B | D3 | H3 | MOR | |

COMPOUND 1

|   | A | B | C | D | E | F |
|---|---|---|---|---|---|---|
| 1 | 67.9 | 12 | 52 | 39 | 36 | 25.9 |
| 2 | 2.2 | 0.5 | 50 | -10.2 | 7.1 | 2.8 |
| 3 | 11.5 | 14.5 | 6.7 | 19.7 | -9 | 10.2 |
| 4 | 4.9 | 16.7 | 48.5 | -7.7 | 0.5 | 95.1 |
| 5 | 33.4 | 16.8 | 8.2 | -5.9 | -15.8 | 51.9 |
| 6 | 88.6 | 26.7 | 21.9 | -12.1 | 0.3 | |
| 7 | 52.4 | 54 | 12.3 | -14.6 | -9.6 | |
| 8 | 7 | 42.7 | 79.7 | 37.6 | -1.5 | |

SELECTIVE D3 DOPAMINE RECEPTOR AGONISTS AND METHODS OF THEIR USE

CROSS REFERENCE TO RELATED APPLICATION

This application is a continuation application of U.S. patent application Ser. No. 16/093,365, filed Oct. 12, 2018, which is a national stage application of PCT/US2017/027618 filed on Apr. 14, 2017, which claims the benefit of U.S. Provisional Patent Application No. 62/322,361 filed on Apr. 14, 2016, both of which are incorporated by reference in their entirety herein.

STATEMENT OF GOVERNMENT SUPPORT

This invention was made in part with government support from the US Department of Health and Human Services, National Institutes of Health. This invention was made with government support under Grant Number HG005031 awarded by the National Institutes of Health. The United States government has certain rights in this invention.

BACKGROUND

G-protein coupled receptors (GPCRs) are among the most intensely investigated drug targets in the pharmaceutical industry. Over 40% of all FDA approved drugs target these important receptor proteins. Unfortunately, many of the ligands that are used as drugs or pharmacological tools are not selective and exhibit some unintended activity on non-target GPCRs or other proteins. This is because the orthosteric binding site is highly conserved among closely related types of GPCRs.

Dopamine receptors (DARs) are G-protein coupled receptors (GPCRs) that play a critical role in cell signaling processes and modulation of information transfer within the nervous system. Five functionally active DARs have been identified in the mammalian genome. The DAR subtypes have profoundly diverse physiological effects. Studies investigating compounds that semi-selectively activate the $D_3$ DAR suggest that $D_3$ activation may elicit important neuroprotection actions. Despite numerous attempts to produce $D_3$ selective modulators, current FDA-approved drugs display relatively poor selectivity between the closely related $D_2$ and $D_3$ DARs. $D_2$ and $D_3$ receptors share 74% homology in their transmembrane spanning domains, and the putative orthosteric binding sites, where the endogenous agonist dopamine (DA) binds, are 94% identical. Therefore, most currently available dopaminergic drugs, including anti-psychotics and anti-Parkinson's disease medications, and research tool compounds that modulate either the $D_2$ or $D_3$ DARs modulate the other subtype to varying degrees.

Studies using semi-selective (i.e., ~10-fold) $D_3/D_2$ DAR orthosteric agonists suggest that $D_3$ DAR activation may have important therapeutic potential. Compounds that stimulate both the $D_2$ DAR and $D_3$ DAR, but have somewhat higher affinity for the $D_3$ DAR, such as the FDA-approved drugs pramipexole and ropinirole, are effective in the treatment of Parkinson's disease and restless legs syndrome (RLS). These compounds are not only clinically active in relieving motor deficits, but also slow the loss of dopaminergic terminals upon long-term administration to patients with Parkinson's disease. Further, in preclinical animal models, $D_3$ DAR-preferring agonists are potent neuroprotective agents. Treatment with $D_3$ DAR-preferring agonists has been shown to decrease the loss of dopaminergic neurons in animals treated with selective toxins that target these cells, and studies with $D_3$ DAR knockout mice support that the neuroprotective effects are mediated directly by the $D_3$ DAR. Pramipexole has also been shown to prevent neurotoxicity induced by oligomers of beta-amyloid and to restore nigrostriatal dopamine in lesioned mice. Although it is difficult to assess neuroprotection in living human subjects, clinical trials assessing the neuroprotective effects of pramipexole in Parkinson's disease have suggested positive effects. $D_3$-preferring ligands have clinical potential in treating Parkinson's disease and related syndromes, dyskinesia, especially dyskinesias secondary to treating Parkinson's disease with L-DOPA, neurodegenerative disorders such as Alzheimer's disease and dementia, restless legs syndrome, depression, schizophrenia, cognitive dysfunction, or substance use disorders, including addiction to alcohol, nicotine, cocaine, methamphetamine and opioids. However, conventional $D_3$-preferring $D_2/D_3$ DAR agonists can induce impulse control disorders, suggesting that $D_2$ DAR stimulation may be involved in this significant side effect. Thus, there is a need for highly selective $D_3$ DAR agonists. This disclosure fulfills this need and provides additional advantages.

SUMMARY

The present disclosure provides a compound of Formula I

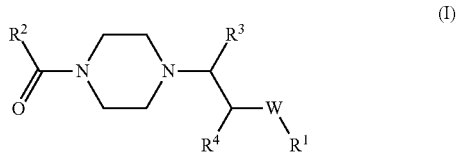

or a pharmaceutically acceptable salt thereof. In Formula I the variables W, $R^1$, and $R^2$ carry the following definitions.

W is O or S.

$R^1$ is aryl or heteroaryl.

$R^2$ is a a phenyl, a 5 or 6-membered heteroaryl, having 1, 2, 3, or 4 heteroatoms independently chosen from N, O, and S or a 6,5-bicyclic heteroaryl group, having 1, 2, 3, 4, 5, or 6 heteroatoms independently chosen from N, O, and S, wherein the point of attachment in Formula I is in the 5-membered ring, and the 5-membered ring contains at least one heteroatom.

$R^1$ and $R^2$ are each substituted with 0 or 1 or more substituents independently chosen from halogen, hydroxyl, cyano, nitro, oxo, —$CONH_2$, amino, mono- and di-$C_1$-$C_4$alkylcarboxamide, ($C_3$-$C_6$cycloalkyl)$C_0$-$C_2$alkyl, and $C_1$-$C_6$hydrocarbyl, which $C_1$-$C_6$hydrocarbyl group is a hydrocarbon chain in which the carbon atoms are joined by single, double or triple bonds, and any one carbon atom can be replaced by O, NH, or N($C_1$-$C_4$alkyl) and which hydrocarbyl group is optionally substituted with one or more substituents independently chosen from hydroxyl, oxo, halogen, and amino.

$R^3$ and $R^4$ are independently hydrogen or methyl.

The disclosure also provides pharmaceutical compositions comprising a compound of Formula I or salt thereof together with a pharmaceutically acceptable carrier.

The disclosure also includes methods of treating Parkinson's disease and related syndromes, dyskinesia, especially dyskinesias secondary to treating Parkinson's disease with L-DOPA, neurodegenerative disorders such as Alzheimer's disease and dementia, Huntington's disease, restless legs syndrome, bipolar disorder and depression, schizophrenia, cognitive dysfunction, or substance use disorders, comprising administering a therapeutically effective amount of a compound or salt of Formula I and at least one pharmaceutically acceptable carrier to a patient in need of such treatment. The compound of Formula I may be the only active compound administered to the patient or may be administered together with one or more additional active agents

BRIEF DESCRIPTION OF THE DRAWINGS

FIG. 2A to FIG. 2C. Graphs of BRET Ratio (% dopamine response, % DA response) versus concentration (molar, M) of test compound or control, wherein FIG. 2A shows BRET arrestin recruitment assay results, FIG. 2B shows $G_o$ BRET activation assay results, and FIG. 2C shows ERK1/2 Phosphorylation assay results.

FIG. 4A shows the legend of GPCRs tested in the panel, FIG. 4B shows full numerical results for Compound 1 in the panel, and FIG. 4C is histogram of the screen and shows that Compound 1 displays affinity only for the D3R, 5-HT1A, 5-HT2B, and Sigmal receptor.

DETAILED DESCRIPTION

Terminology

Figure 1:
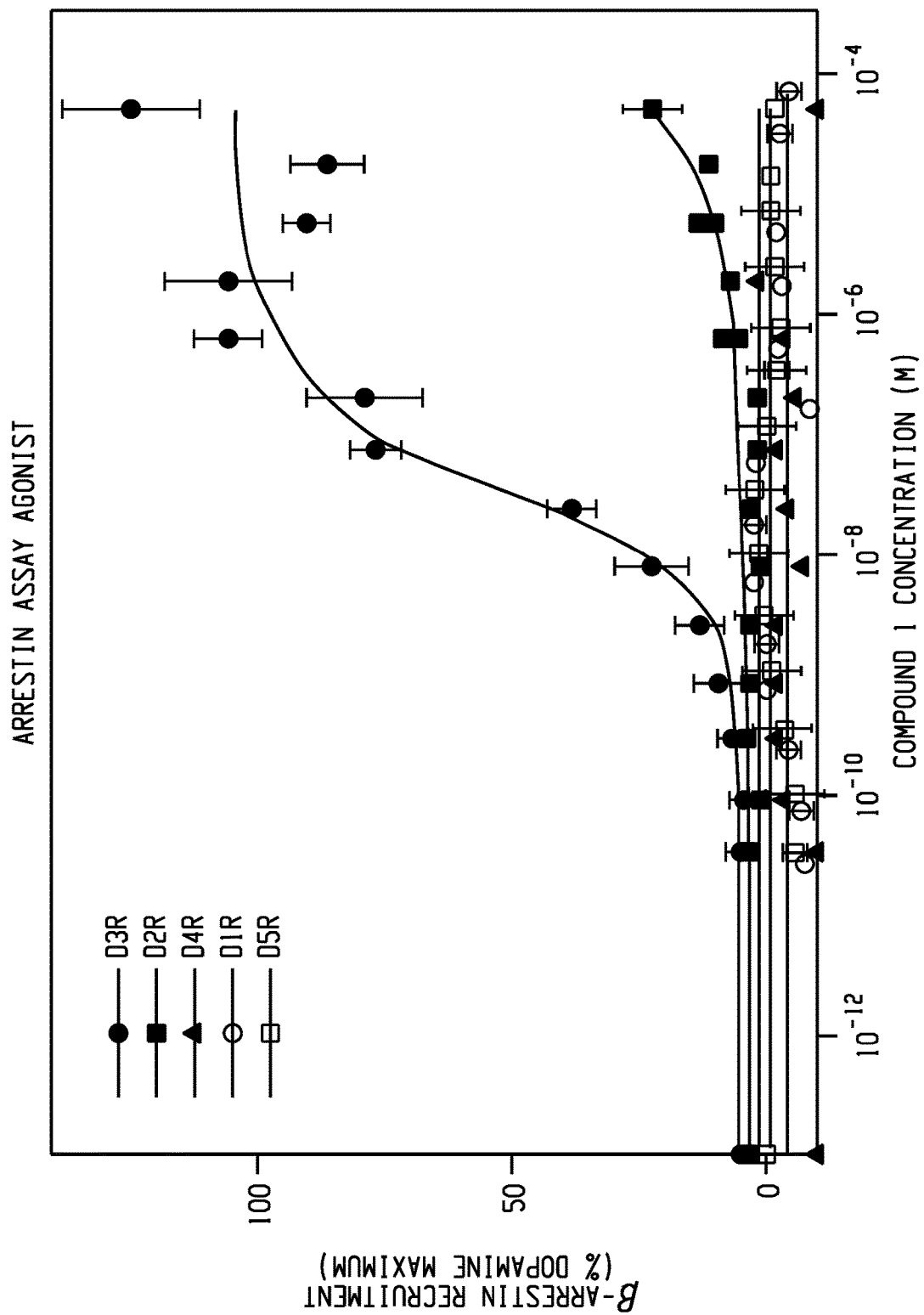
FIG. 1. A graph of β-arrestin recruitment (% dopamine maximum) versus concentration of Compound 1 (molar, M) illustrating concentration-response curves for Compound 1 in an arrestin recruitment agonist assay for the D1, D2, D3, D4, and D5 receptors.
Figure 2A:
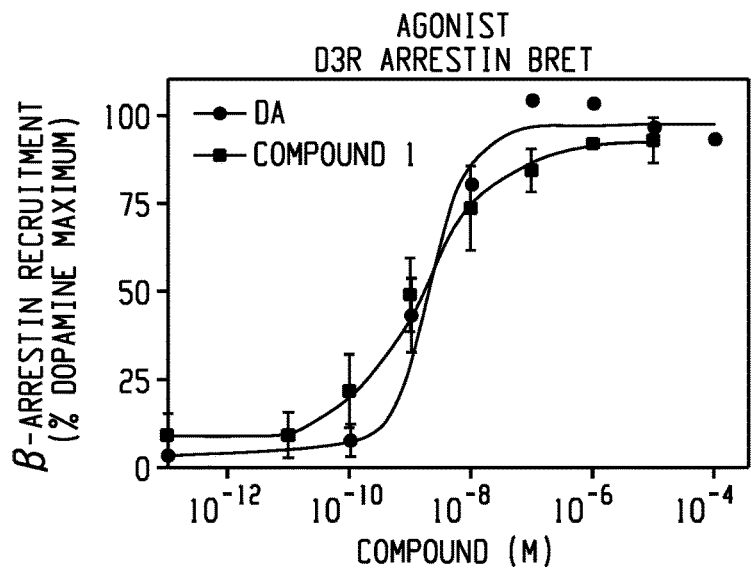
Figure 2A:
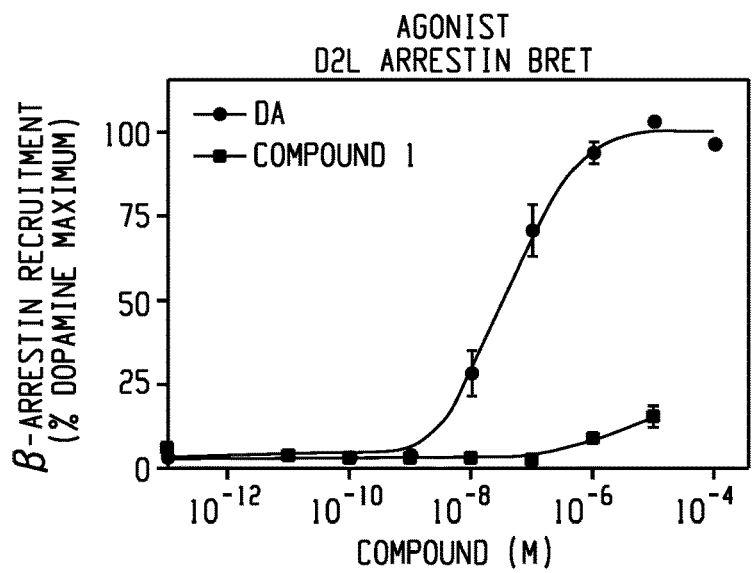
Figure 2A:
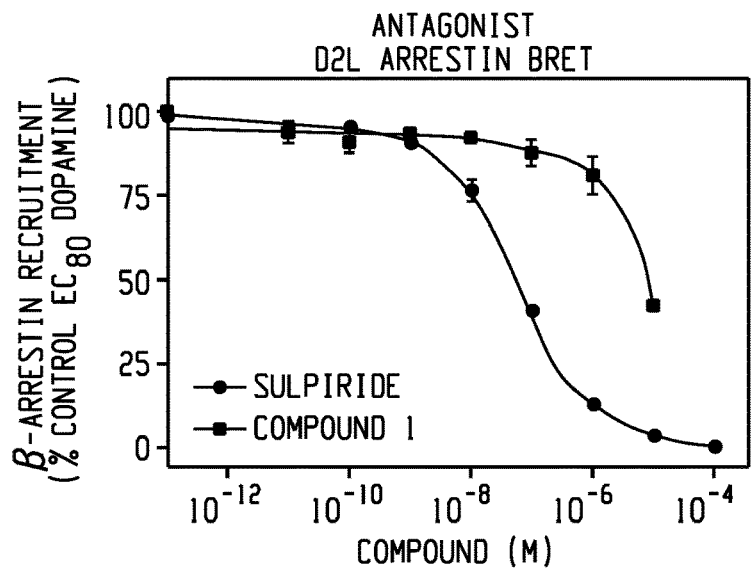
Figure 2B:
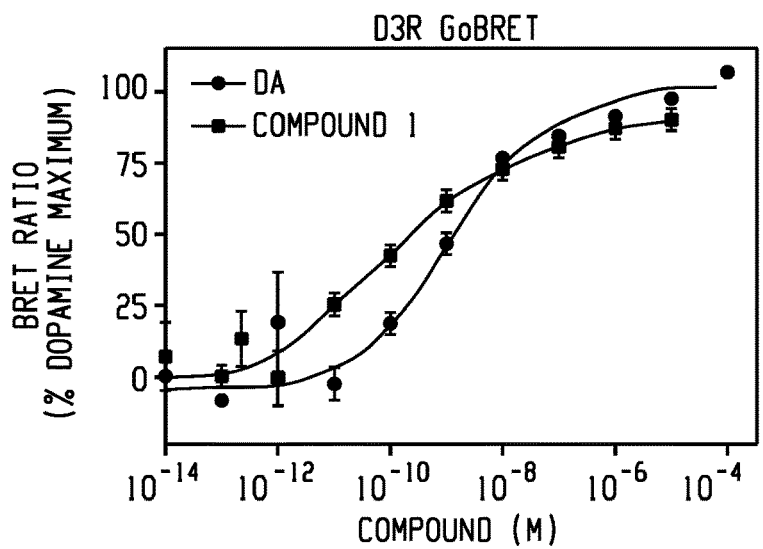
Figure 2B:
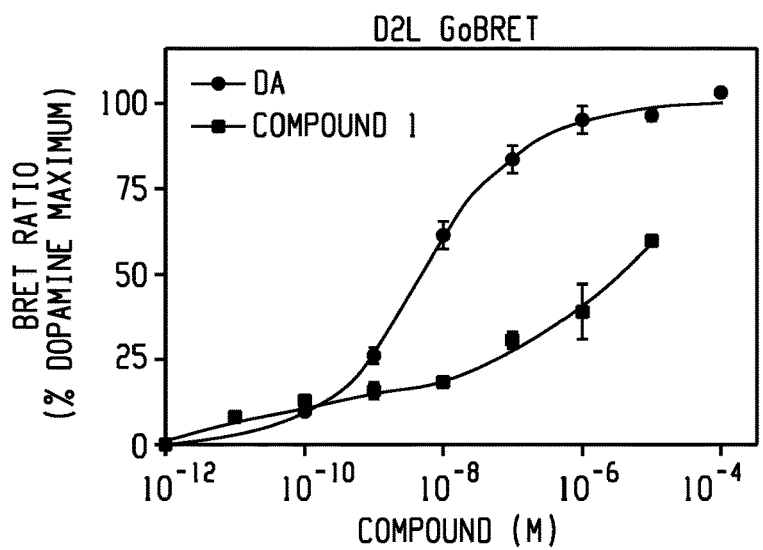
Figure 2B:
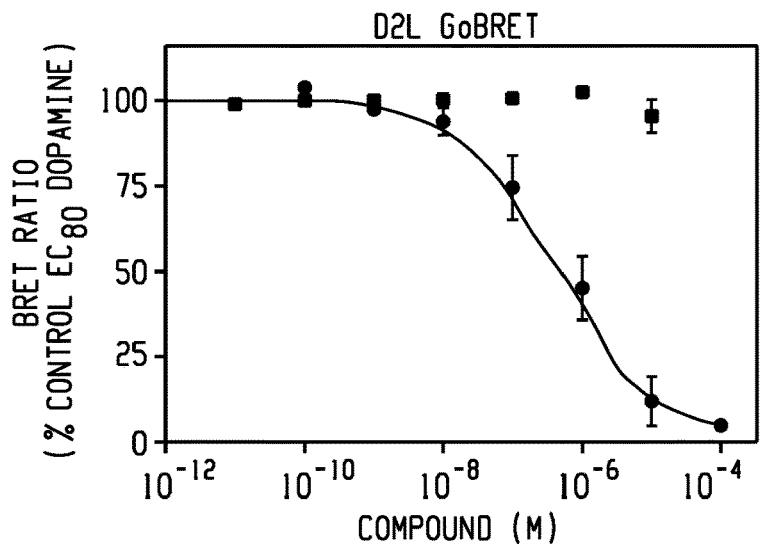
Figure 2C:
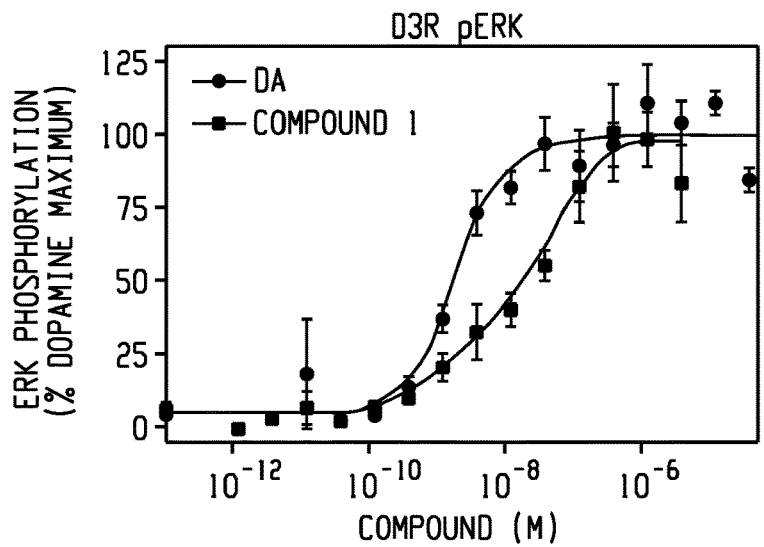
Figure 2C:
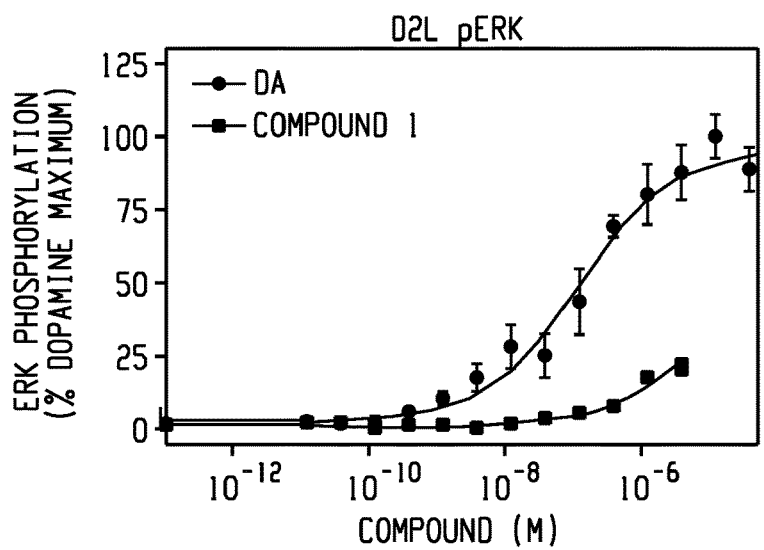
Figure 2C:
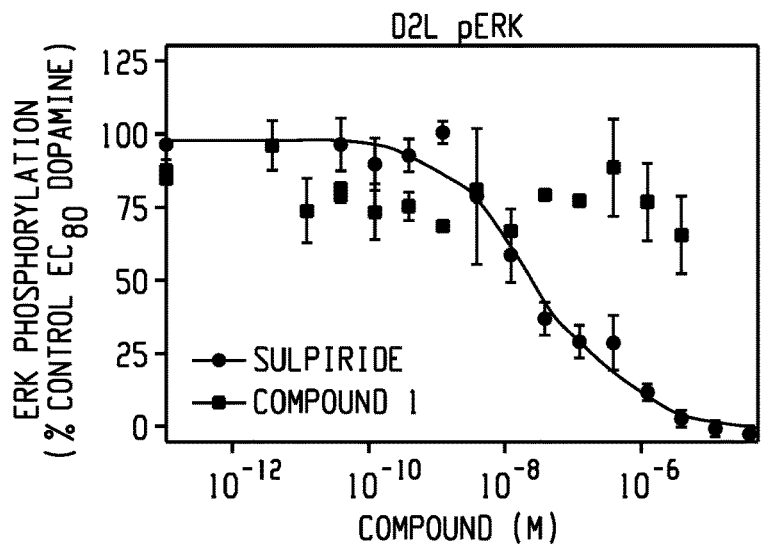

Compounds of the present disclosure are generally described using standard nomenclature.

The terms "a" and "an" do not denote a limitation of quantity, but rather denote the presence of at least one of the referenced item. The term "or" means "and/or." The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on its scope unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this disclosure belongs.

"Formula I" includes compounds and salts of certain subformulae.

In certain situations, the compounds of Formula I may contain one or more asymmetric elements such as stereogenic centers, stereogenic axes and the like, e.g. asymmetric carbon atoms, so that the compounds can exist in different stereoisomeric forms. Formula I includes all stereoisomeric forms, including racemates, optically enriched, and optically pure forms. In addition, compounds with carbon-carbon double bonds may occur in Z- and E-forms, with all isomeric forms of the compounds being included in the present disclosure. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The disclosure of Formula I include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$ and isotopes of fluorine including $^{19}F$.

Certain compounds are described herein using a general formula that includes variables, e.g. W, $R^1$, and $R^2$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

Combinations of substituents and/or variables are permissible only if such combinations result in stable compounds. A stable compound or stable structure is meant to imply a compound that is sufficiently robust to survive isolation from a reaction mixture, and subsequent formulation into an effective therapeutic agent.

The term "substituted" means that any one or more hydrogen atoms bound to the designated atom or group is replaced with a selection from the indicated group, provided that the designated atom's normal valence is not exceeded. Unless otherwise specified substituents are named into the core structure. For example, it is to be understood that when (cycloalkyl)alkyl is listed as a possible substituent the point of attachment of this substituent to the core structure is in the alkyl portion.

Substituents are named into the ring unless otherwise indicated. A dash ("-") or a double bond ("=") that is not between two letters or symbols indicates the point of attachment for a substituent. For example, —CONH$_2$ is attached through the carbon atom.

An "active agent" means a compound (including a compound disclosed herein), element, or mixture that when administered to a patient, alone or in combination with another compound, element, or mixture, confers, directly or indirectly, a physiological effect on the subject. The indirect physiological effect may occur via a metabolite or other indirect mechanism. The "active agent" may also potentiate, or make more active another active agent. For example the compounds of Formula I potentiate the activity of other active agents when given in combination with another active agent, for example by lowering the effective dose of the other active agent.

An "aliphatic group" is a non-aromatic hydrocarbon group having the indicated number of carbon atoms. Aliphatic groups may be saturated, unsaturated, or cyclic.

"Alkyl" includes both branched and straight-chain saturated aliphatic hydrocarbon groups, having the specified number of carbon atoms. Thus, the term $C_1$-$C_6$alkyl includes alkyl groups having from 1 to about 6 carbon atoms. When $C_0$-$C_n$alkyl is used herein in conjunction with another group, for example, (cycloalkyl)$C_0$-$C_2$ alkyl, the indicated group, in this case cycloalkyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl. $C_1$-$C_6$alkyl includes alkyl groups having 1, 2, 3, 4, 5, or 6 carbon atoms.

"Alkoxy" is an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" is an alkyl group as defined above with the indicated number of carbon atoms covalently bound to the group it substitutes through a carbonyl (C=O) bridge. The carbonyl carbon is included in the number of carbons, that is $C_2$alkanoyl is a $CH_3$(C=O)— group.

"Alkylester" is an alkyl group as defined herein covalently bound to the group it substitutes by an ester linkage. The ester linkage may be in either orientation, e.g., a group of the formula —O(C=O)alkyl or a group of the formula —(C=O)Oalkyl.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl, naphthyl, including 1-naphthyl, 2-naphthyl, and bi-phenyl.

"Mono- and/or di-alkylamino" are secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino. A "(mono- and/or di-alkylamino)$C_0$-$C_2$alkyl group is a mono and/or dialkylamino group as defined that is directly bound to the group it substitutes ($C_0$alkyl) or attached to the group it substitutes via a 1 to 2 carbon alkyl group linker.

"Cycloalkyl" is a saturated hydrocarbon ring groups, having the specified number of carbon atoms, usually from 3 to 7 carbon atoms. Examples of cycloalkyl groups include cyclopropyl, cyclobutyl, cyclopentyl, or cyclohexyl as well as bridged or caged saturated ring groups such as norborane or adamantane. In the term "(cycloalkyl)alkyl," cycloalkyl and alkyl are as defined above, and the point of attachment in on the alkyl group.

"Halo" or "halogen" as used herein refers to fluoro, chloro, bromo, or iodo.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

A "hydrocarbyl" group is a hydrocarbon chain having the specified number of carbon atoms in which carbon atoms are joined by single, double or triple bonds, and any one carbon atom can be replaced by O, NH, or N($C_1$-$C_4$alkyl).

"Pharmaceutical compositions" are compositions comprising at least one active agent, such as a compound or salt of Formula I and at least one other excipient. "Carriers" are any inactive materials, including excipients and diluents, which may be added to the pharmaceutical compositions including carriers and diluents. Pharmaceutical compositions meet the U.S. FDA's GMP (good manufacturing practice) standards for human or non-human drugs.

"Pharmaceutically acceptable salts" includes derivatives of the disclosed compounds wherein the parent compound is modified by making non-toxic acid or base salts thereof, and further refers to pharmaceutically acceptable hydrates or solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

The term "carrier" applied to pharmaceutical compositions/combinations of the invention refers to a diluent, excipient, or vehicle with which an active compound is provided.

A "patient" is a human or non-human animal in need of medical treatment. In some embodiments the patient is a human patient.

The term "therapeutically effective amount" of a compound of Formula I, or a related formula, means an amount effective, when administered to a patient, to provide a therapeutic benefit such as an amelioration of symptoms, e.g., an amount effective to decrease the symptoms of a central nervous system disorder, and including an amount sufficient to reduce the symptoms of Parkinson's disease, restless legs syndrome, bipolar disorder, hyperprolactinemia, depression, Huntington's chorea, Alzheimer's disease, or the cravings associated with substance abuse. Thus a therapeutically effective amount of a compound is also an amount sufficient to significantly reduce the indicia of the disease or condition being treated. A significant reduction is any detectable negative change that is statistically significant in a standard parametric test of statistical significance, such as Student's t-test, in which p<0.05.

Chemical Description

This disclosure provides compounds of Formula I, certain of which exhibit high selectivity for functionally activating the $D_3$ DAR. In one embodiment, certain compounds of Formula I promote β-arrestin translocation to the $D_3$ DAR with an $EC_{50}$ of less than 200 nM and in some embodiments less than 50 nM and can have an efficacy equal to that of dopamine. Certain compounds of Formula I that promote β-arrestin translocation to the $D_3$ DAR with an $EC_{50}$ of less than 200 nM also exhibit minimal effects on $D_2$ DAR-mediated β-arrestin translocation. Certain compounds of Formula I also lack agonist activity at the $D_2$ DAR as assessed using a [35S]GTPγS binding assay. Certain compounds of Formula I also exhibit potent agonist activity in $D_3$ DAR G protein-mediated signaling responses as demonstrated using a Go-BRET assay and ERK1/2 phosphorylation assay. Certain compounds of Formula I have no functional activity at other DAR subtypes except for minimal $D_2$ DAR inhibition at concentrations over 10 μM. Using the β-arrestin translocation assay as an exemplary functional output to screen 168 different G protein-coupled receptors (GPCRs), certain compounds of Formula I exhibit extreme selectivity for activating the $D_3$ DAR with minimal to no activation of other receptors. Certain compounds of Formula I also exhibit extreme selectivity for the $D_3$ DAR as assessed in a panel of radioligand binding assays. Certain compounds of Formula I do not compete for orthosteric radioligand binding to the $D_3$ DAR at concentrations that produce maximal functional stimulation. Without wishing to be bound to any particular theory, these radioligand binding assays suggest that compounds of Formula I exhibit high selectivity and efficacy due to their interaction with the $D_3$ DAR in a highly unique fashion. Molecular modeling studies and site-directed mutagenesis suggest certain compounds of Formula I bind to the $D_3$ DAR in a manner district from the $D_2$ DAR. Using a neuronal cell culture assay to assess neuroprotective properties against a toxin of monoaminergic neurons, compounds of Formula I exhibit neuroprotection with an efficacy greater than that of pramipexole, a much less selective agonist of the $D_3$ DAR.

In addition to compounds and salts of Formula I disclosed in the SUMMARY section, the disclosure includes compounds and salts of Formula I

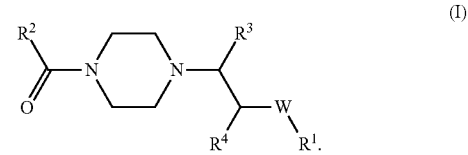

(I)

in which the variables may carry any of the values set forth below. The disclosure includes any combination of the variable definitions so long as a stable compound that is within the scope of Formula (I) results.

(1) $R^3$ and $R^4$ are both hydrogen.

(2) One of $R^3$ and $R^4$ is methyl and the other is hydrogen.

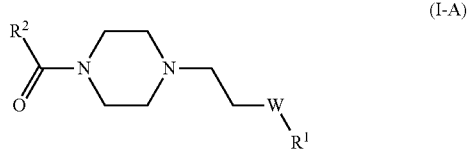

(I-A)

(3) Formula I-A $R^2$ is a 6,5-bicyclic heteroaryl group, having 1, 2, 3, 4, 5, or 6 heteroatoms independently chosen from N, O, and S, wherein the point of attachment in Formula I is in the 5-membered ring, and the 5-membered ring contains at least one heteroatom; where substituted with 0 or 1 or more substituents independently chosen from halogen, hydroxyl, cyano, nitro, oxo, —$CONH_2$, amino, mono- and di-$C_1$-$C_4$alkylcarboxamide, ($C_3$-$C_6$cycloalkyl)$C_0$-$C_2$alkyl, and $C_1$-$C_6$hydrocarbyl, which $C_1$-$C_6$hydrocarbyl group is a hydrocarbon chain in which the carbon atoms are joined by single, double or triple bonds, and any one carbon atom can be replaced by O, NH, or N($C_1$-$C_4$alkyl) and which hydrocarbyl group is optionally substituted with one or more substituents independently chosen from hydroxyl, oxo, halogen, and amino.

(4) $R^2$ is a 6,5-bicyclic heteroaryl group selected from the following optionally substituted 6,5-bicyclic heteroaryl groups:

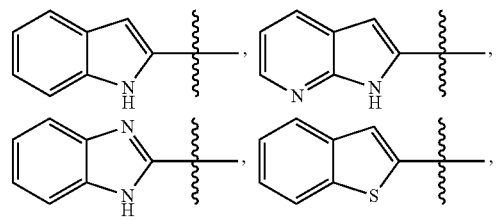

-continued

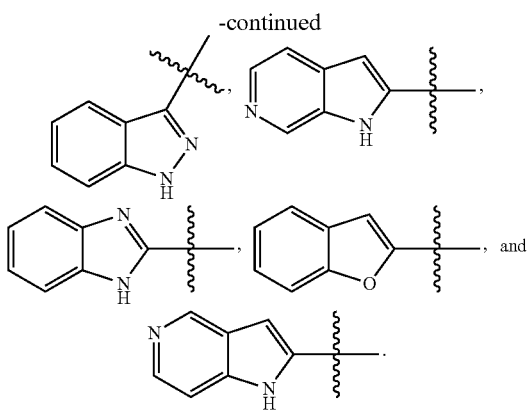

(5) $R^2$ is a phenyl, 2-pyridyl, 3-pyridyl, 4-pyridyl, or pyrolyl group, each of which is optionally substituted.

(6) $R^2$ is a 6,5-bicyclic heteroaryl group substituted with 0 or 1 or more substituents independently chosen from halogen, hydroxyl, cyano, nitro, —$CONH_2$, amino, $C_1$-$C_6$alkyl, $C_1$-$C_6$alkoxy, $C_2$-$C_4$alkanoyl, $C_1$-$C_4$alkylester mono- and di-$C_1$-$C_4$alkylamino, mono- and di-$C_1$-$C_4$alkylcarboxamide, ($C_3$-$C_6$cycloalkyl)$C_0$-$C_2$alkyl, and any one carbon atom in a $C_1$-$C_6$alkyl or $C_1$-$C_6$alkoxy can be replaced by O, NH, or N($C_1$-$C_4$alkyl) and which $C_1$-$C_6$alkyl or $C_1$-$C_6$alkoxy is optionally substituted with one or more substituents independently chosen from hydroxyl, halogen, and amino.

(7) $R^2$ is

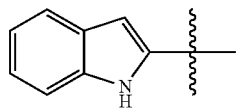 [SMILES: *c1cc2ccccc2[nH]1]

which is substituted with 0 or 1 or more substituents independently chosen from halogen, hydroxyl, cyano, nitro, —$CONH_2$, amino, $C_1$-$C_6$alkyl, $C_1$-$C_6$alkoxy, $C_2$-$C_4$alkanoyl, $C_1$-$C_4$alkylester mono- and di-$C_1$-$C_4$alkylamino, mono- and di-$C_1$-$C_4$alkylcarboxamide, ($C_3$-$C_6$cycloalkyl)$C_0$-$C_2$alkyl, and any one carbon atom in a $C_1$-$C_6$alkyl or $C_1$-$C_6$alkoxy can be replaced by O, NH, or N($C_1$-$C_4$alkyl) and which $C_1$-$C_6$alkyl or $C_1$-$C_6$alkoxy is optionally substituted with one or more substituents independently chosen from hydroxyl, oxo, halogen, and amino.

(8) $R^2$ is a 6,5-bicyclic heteroaryl group substituted with 0 or 1 to 3 substituents independently selected from halogen, $C_1$-$C_2$alkyl, and $C_1$-$C_2$alkoxy.

(9) W is S.

(10) W is O.

(11) $R^1$ is phenyl or a monocyclic heteroaryl group having 1, 2, 3 or 4 heteroatoms independently chosen from N, O, and S, each of which $R^1$ is optionally substituted.

(12) $R^1$ is phenyl or pyridyl, each of which is optionally substituted.

(13) $R^1$ is a phenyl or pyridyl, each of which is fused to a 5-membered heterocyclic ring, each of which $R^1$ is optionally substituted.

(14) $R^1$ is optionally substituted indole.

(15) The composition of any one of embodiments 1 to 11, wherein
$R^1$ is substituted with 0 or 1 or more substituents independently chosen from halogen, hydroxyl, cyano, nitro, —$CONH_2$, amino, $C_1$-$C_6$alkyl, $C_1$-$C_6$alkoxy, $C_2$-$C_4$alkanoyl, $C_1$-$C_4$alkylester mono- and di-$C_1$-$C_4$alkylamino, mono- and di-$C_1$-$C_4$alkylcarboxamide, ($C_3$-$C_6$cycloalkyl)$C_0$-$C_2$alkyl, and any one carbon atom in a $C_1$-$C_6$alkyl or $C_1$-$C_6$alkoxy can be replaced by O, NH, or N($C_1$-$C_4$alkyl) and which $C_1$-$C_6$alkyl or $C_1$-$C_6$alkoxy is optionally substituted with one or more substituents independently chosen from hydroxyl, halogen, and amino.

(16) $R^1$ is substituted with 0 or 1 to 3 substituents independently chosen from halogen, $C_1$-$C_2$alkyl, and $C_1$-$C_2$alkoxy.

(17) $R^1$ is 3-pyridyl.

(18) $R^1$ is 4-methoxy-phenyl.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent or may be combined with one or more additional active agents. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I.

Compounds disclosed herein may be administered orally, topically, parenterally, by inhalation or spray, sublingually, transdermally, via buccal administration, or by other means routine in the art for administering pharmaceutical compositions. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

Methods of Treatment

The disclosure provides methods of treating central nervous system disorders, including Parkinson's disease and related syndromes, dyskinesia, especially dyskinesias secondary to treating Parkinson's disease with L-DOPA, neurodegenerative disorders such as Alzheimer's disease and dementia, Huntington's disease, restless legs syndrome, bipolar disorder and depression, schizophrenia, cognitive dysfunction, or substance use disorders comprising administering an effective amount of a compound of Formula I to a patient having one of these disorders.

A compound of Formula I may be the only active agent administered (monotherapy) or may be combined with one or more other active agents (combination, adjunct, or augmentation therapy).

In another embodiment the invention provides a method of treating depression comprising (i) diagnosing a patient as having depression and (ii) providing an effective amount of compound of Formula I to the patient, wherein the compound of Formula I is provided as the only active agent or is provided together with one or more additional active agents.

Psychosocial intervention may play an important role in treatment of any central nervous system disorder. Psychosocial intervention includes cognitive-behavior therapy, dialectical-behavior therapy, interpersonal therapy, psychodynamic therapy, and group therapy. In another embodiment, the disclosure provides a method of treating a central nervous system disorder in a patient including administration of an effective amount of a compound of Formula I to the patient, the method further including providing psychosocial intervention to the patient.

In another embodiment the disclosure provides a method to slow or reverse the progressive loss of neurons seen in Parkinson's disease, Alzheimer's disease, or other disorders involving neurodegeneration, by providing an effective amount of compound of Formula I to the patient, wherein the compound of Formula I is provided as the only active agent or is provided together with one or more additional active agents. For example an effective amount of a compound of Formula I is an amount sufficient to decrease depression symptoms or Parkinson's disease symptoms. Preferably the decrease in depression symptoms or Parkinson's disease symptoms is a 50% or greater reduction of symptoms identified on symptom rating scale for these disorders. For example an effective amount may be an amount sufficient to decrease the patient's score on a psychiatric symptoms rating scale such as the Brief Psychiatric Rating Scale, the Clinical Global Impression, or the Positive and Negative Syndrome Scale or the Movement Disorder Society Unified Parkinson's Disease Rating Scale (MDS-UPDRS).

Examples

General Methods for Chemistry

All reagents were used as received from the following suppliers: Alfa Aesar, Ark Pharm, Aldrich, and Fisher Scientific. Acetonitrile and THF were purified using the Innovative Technology PureSolv solvent purification system. The $^1$H and $^{13}$C NMR spectra were recorded on either a Bruker Avance 400 MHz or 500 MHz spectrometer. Chemical shifts are reported in parts per million and were referenced to residual proton solvent signals. When indicated, $^{13}$C multiplicities were determined with the aid of an APT pulse sequence, differentiating the signals for methyl and methane carbons as "d" from methylene and quarternary carbons as "u".

The infrared (IR) spectra were acquired as thin on a PerkinElmer Spectrum One FT-IR spectrometer equipped with a universal ATR sampling accessory and the absorption frequencies are reported in cm$^{-1}$.

Flash column chromatography separations were performed using the Teledyne Isco CombiFlash R$_F$ using RediSep R$_F$ silica gel columns. TLC was performed on Analtech UNIPLATE silica gel GHLF plates (gypsum inorganic hard layer with fluorescence). TLC plates were visualized under a long wave/short wave UV lamp.

Automated preparative RP HPLC purification was performed using an Agilent 1200 Mass-Directed Fractionation system (Prep Pump G1361 with gradient extension, make-up pump G1311A, pH modification pump G1311A, HTS PAL autosampler, UV-DAD detection G1315D, fraction collector G1364B, and Agilent 6120 quadrapole spectrometer G6120A).

The preparative chromatography conditions included a Waters X-Bridge C18 column (19×150 mm, 5 µm, with 19×10-mm guard column), elution with a water and acetonitrile gradient, which increases 20% in acetonitrile content over 4 min at a flow rate of 20 mL/min (modified to pH 9.8 through addition of NH$_4$OH by auxiliary pump), and sample dilution in DMSO. The preparative gradient, triggering thresholds, and UV wavelength were selected according to the analytical RP HPLC analysis of each crude sample. The analytical method used an Agilent 1200 RRLC system with UV detection (Agilent 1200 DAD SL) and mass detection (Agilent 6224 TOF). The analytical method conditions included a Waters Aquity BEH C$_{18}$ column (2.1×50 mm, 1.7 µm) and elution with a linear gradient of 5% acetonitrile in pH 9.8 buffered aqueous ammonium formate to 100% acetonitrile at 0.4 mL/min flow rate.

Compound purity was measured on the basis of peak integration (area under the curve) from UV/Vis absorbance (at 214 nm), and compound identity was determined on the basis of mass analysis. All compounds used for biological studies have purity >90%.

Example 1. Synthesis of (1H-indol-2-yl)(4-(2-(4-methoxyphenoxy)ethyl)piperazin-1-yl)methanone (Compound 1)

Scheme I

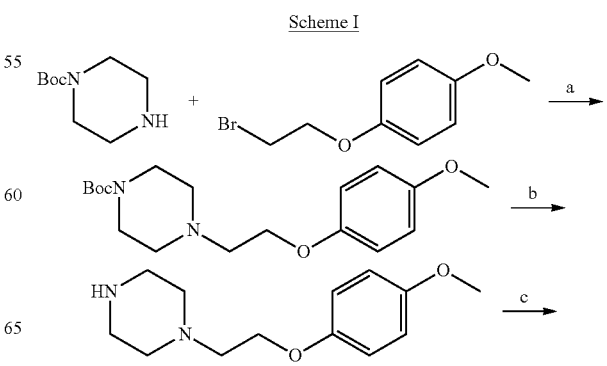

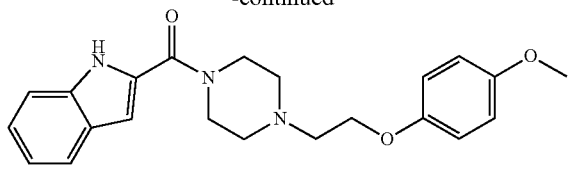

Compound 1 was prepared according to the method shown in Scheme I. Reagents and conditions: a) K$_2$CO$_3$, potassium iodide, MeCN, 70° C.; b) CF$_3$CO$_2$H, Et$_3$SiH, CH$_2$Cl$_2$, rt; c) PyBop, i-Pr$_2$EtN, indole-2-carboxylic acid, DMF, rt.

Step 1. Synthesis of tert-Butyl 4-(2-(4-methoxyphenoxy) ethyl)piperazine-1-carboxylate (Reaction a). A mixture of tert-butyl piperazine-1-carboxylate (490 mg, 2.63 mmol), 1-(2-bromoethoxy)-4-methoxybenzene (608 mg, 2.63 mmol), potassium carbonate (727 mg, 5.26 mmol) and potassium iodide (44 mg, 0.263 mmol) in acetonitrile (35 mL) was heated at 70° C. for 16 h. The reaction was cooled to rt, filtered and the solids washed with acetonitrile (2×15 mL). The combined organics were adsorbed onto celite and purified by silica chromatography to afford the ether product as a colorless oil (622 mg, 1.85 mmol, 70% yield). R$_f$=0.57 (EtOAc); $^1$H NMR (400 MHz, CDCl$_3$) δ 1.46 (s, 9H), 2.51 (t, J=4.8 Hz, 4H), 2.79 (t, J=6.0 Hz, 2H), 3.45 (t, J=4.8 Hz, 4H), 3.76 (s, 3H), 4.05 (t, J=6.0 Hz, 2H), 6.83 (d, J=2.4 Hz, 4H); $^{13}$C NMR (101 MHz, APT pulse sequence, CDCl$_3$) δ d 28.5, 55.8, 114.7, 115.7; u 53.5, 57.5, 66.7, 79.6, 153.0, 154.1, 154.8; HRMS (m/z): calcd. for C$_{18}$H$_{29}$N$_2$O$_4$ [M+H]$^+$ 337.2122; found 337.2122; HPLC purity: 99.0%.

Step 2. 1-(2-(4-Methoxyphenoxy)ethyl)piperazine. To a solution of tert-butyl 4-(2-(4-methoxyphenoxy)ethyl)piperazine-1-carboxylate (185 mg, 0.55 mmol) and triethylsilane (96 mg, 0.825 mmol) in CH$_2$Cl$_2$ (5 mL) was added trifluoroacetic acid (0.85 mL, 1,254 mg, 11.00 mmol). The reaction was stirred at rt for 4 h and concentrated under vacuum. The residue was partitioned between aqueous sodium bicarbonate (10 mL) and CH$_2$Cl$_2$ (3×10 mL). The combined organic layers were concentrated under vacuum to afford the piperazine product as a colorless oil (118 mg, 0.499 mmol, 91% yield). $^1$H NMR (400 MHz, CDCl$_3$) δ 2.54-2.60 (m, 4H), 2.78 (t, J=6.0 Hz, 2H), 2.94 (t, J=4.8 Hz, 4H), 3.76 (s, 3H), 4.05 (t, J=6.0 Hz, 2H), 6.83 (d, J=2.8 Hz, 4H); $^{13}$C NMR (101 MHz, APT pulse sequence, CDCl$_3$) δ d 55.8, 114.8, 115.7; u 45.9, 54.6, 58.0, 66.6, 153.0, 154.0; HRMS (m/z): calcd. for C$_{13}$H$_{21}$N$_2$O$_2$ [M+H]$^+$ 237.1598; found 237.1573; HPLC purity: 94.1%.

Step 3. (1H-Indol-2-yl)(4-(2-(4-methoxyphenoxy)ethyl) piperazin-1-yl)methanone (Compound 1). To a mixture of 1-(2-(4-methoxyphenoxy)ethyl)piperazine (146 mg, 0.618 mmol), indole-2-carboxylic acid (119 mg, 0.741 mmol) and DMAP (8 mg, 0.062 mmol) in THF (10 mL) was added diisopropylcarbodiimide (0.29 mL, 234 mg, 1.85 mmol). The reaction was stirred at rt for 15 h and the solvents removed under vacuum. The residue was purified via silica gel chromatography with CH$_2$Cl$_2$/(MeOH containing 2% NH$_4$OH) to afford the title compound as an off-white solid. Mp=163-165° C.; R$_f$=0.54 (MeOH (10%) and NH$_4$OH (2%) in CH$_2$Cl$_2$); $^1$H NMR (500 MHz, CDCl$_3$) δ 2.68 (t, J=5.0 Hz, 4H), 2.85 (t, J=5.5 Hz, 2H), 3.77 (s, 3H), 3.91-4.06 (m, 4H), 4.10 (t, J=5.5 Hz, 2H), 6.78 (s, 1H), 6.83-6.87 (m, 3H), 7.12-7.15 (m, 1H), 7.26-7.30 (m, 2H), 7.43 (d, J=8.5 Hz, 1H), 7.65 (d, J=8.0 Hz, 1H), 9.25 (br s, 1H); $^{13}$C NMR (125 MHz, CDCl$_3$) δ 41.0, 53.6, 55.7, 57.3, 66.5, 105.2, 111.7, 114.6, 115.6, 120.6, 121.8, 124.4, 127.4, 129.2, 135.5, 152.8, 154.0, 162.2; HRMS (m/z): calcd. for C$_{22}$H$_{26}$N$_3$O$_3$ [M+H]$^+$ 380.1969; found 380.1995; HPLC purity: 95.6%; FTIR (neat): 3258, 1597, 1506, 1437 cm$^{-1}$.

Example 2. Additional Dopamine D$_3$ Receptor Agonists

The compounds of Formula I shown in Table 1 were prepared by the methods shown in Example 1 for the preparation of Compound 1.

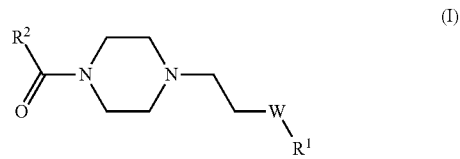

TABLE 1

| Cmpd. No. | —W—R$^1$ | R$^2$ |
|---|---|---|
| 2 | ![phenoxy] | ![indol-2-yl] |
| 3 | ![pyridin-3-yloxy] | ![indol-2-yl] |
| 4 | ![pyridin-3-yloxy] | ![7-azaindol-2-yl] |

TABLE 1-continued
Additional Compounds
| Cmpd. No. | —W—R¹ | R² |
|---|---|---|
| 5 | 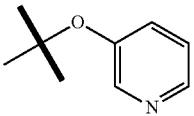 | 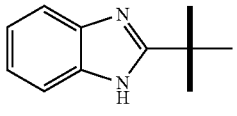 |
| 6 | 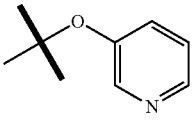 | 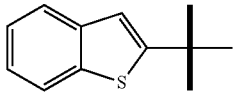 |
| 7 | 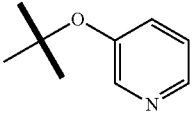 | 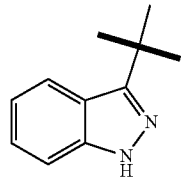 |
| 8 | 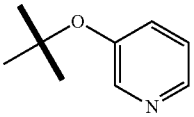 | 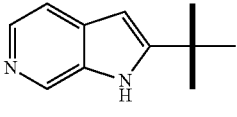 |
| 9 | 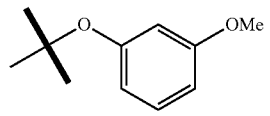 | 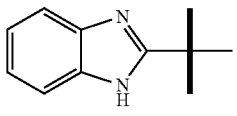 |
| 10 | 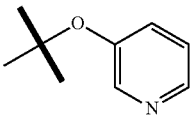 | 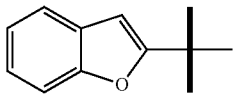 |
| 11 | 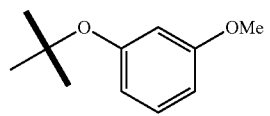 | 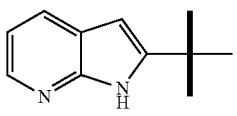 |
| 12 | 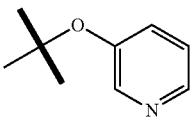 | 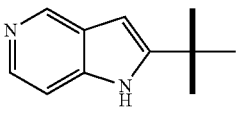 |
| 13 | 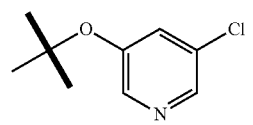 | 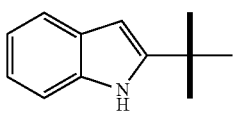 |
| 14 | 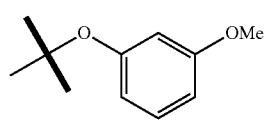 | 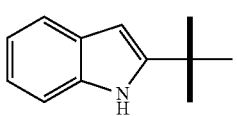 |
| 15 | 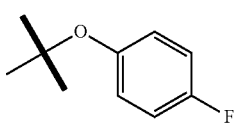 | 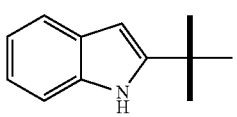 |

TABLE 1-continued
Additional Compounds
| Cmpd. No. | —W—R¹ | R² |
|---|---|---|
| 16 | 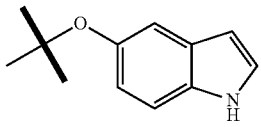 | 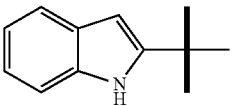 |
| 17 | 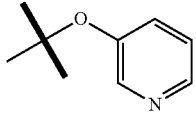 | 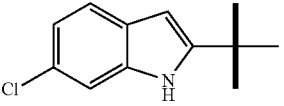 |
| 18 | 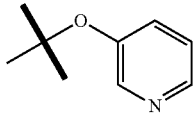 | 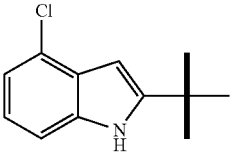 |
| 19 | 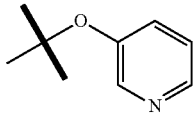 | 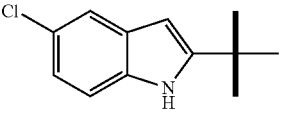 |
| 20 | 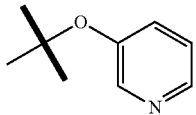 | 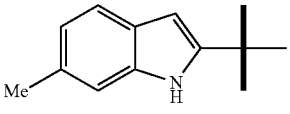 |
| 21 | 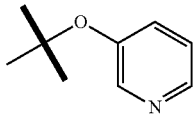 | 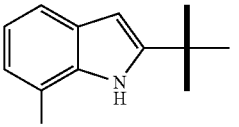 |
| 22 | 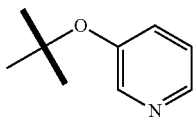 | 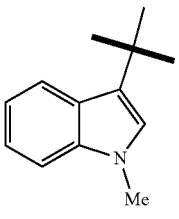 |
| 23 | 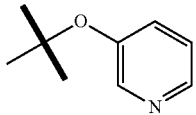 | 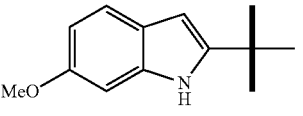 |
| 24 | 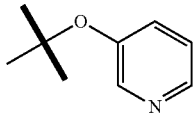 | 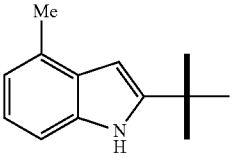 |
| 25 | 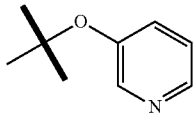 | 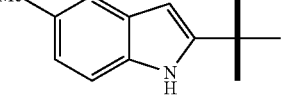 |

TABLE 1-continued
Additional Compounds
| Cmpd. No. | —W—R¹ | R² |
|---|---|---|
| 26 | 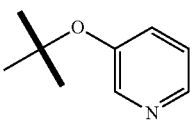 | 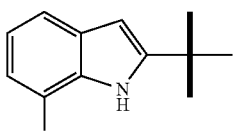 |
| 27 | 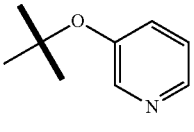 | 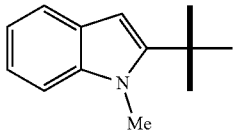 |
| 28 | 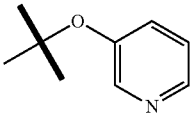 | 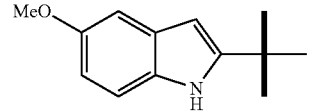 |
| 29 | 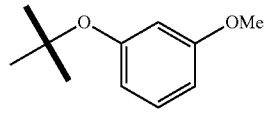 | 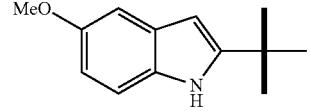 |
| 30 | 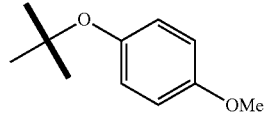 | 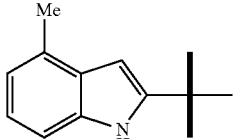 |
| 31 | 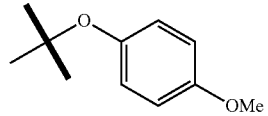 | 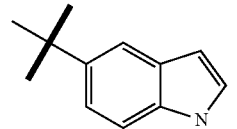 |
| 32 | 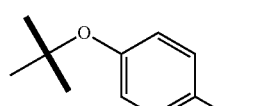 | 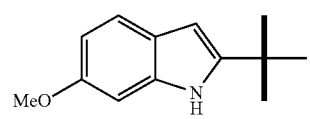 |
| 33 | 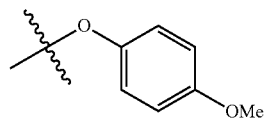 [SMILES: *Oc1ccc(OC)cc1] | 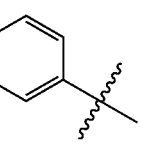 |
| 34 | 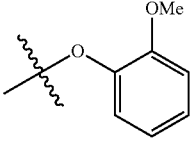 [SMILES: *Oc1ccccc1OC] | 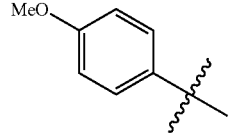 |
| 35 | 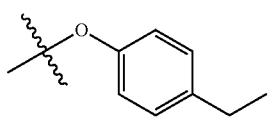 [SMILES: *Oc1ccc(CC)cc1] | 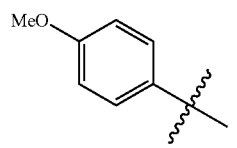 |

TABLE 1-continued
Additional Compounds
| Cmpd. No. | —W—R¹ | R² |
|---|---|---|
| 36 | 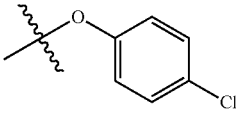 [SMILES: *Oc1ccc(Cl)cc1] | 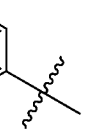 |
| 37 | 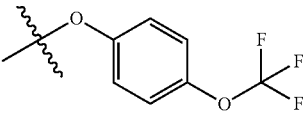 [SMILES: *Oc1ccc(OC(F)(F)F)cc1] | 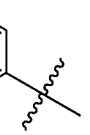 |
| 38 | 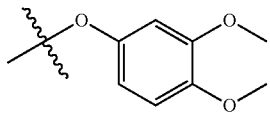 [SMILES: *Oc1ccc(OC)c(OC)c1] | 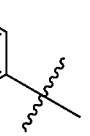 |
| 39 | 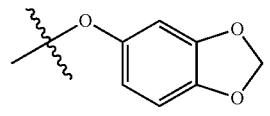 [SMILES: *Oc1ccc2c(c1)OCO2] |  |
| 40 | 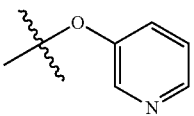 [SMILES: *Oc1cccnc1] |  |
| 41 | 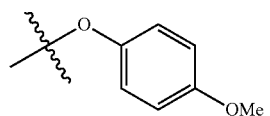 [SMILES: *Oc1ccc(OC)cc1] | 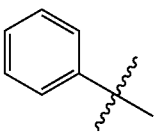 [SMILES: *c1ccccc1] |
| 42 | 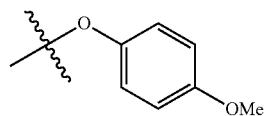 [SMILES: *Oc1ccc(OC)cc1] | 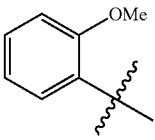 |
| 43 | 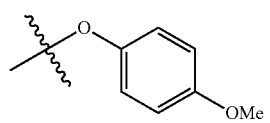 [SMILES: *Oc1ccc(OC)cc1] | 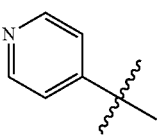 |
| 44 | 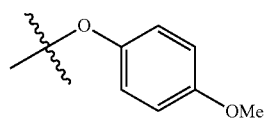 [SMILES: *Oc1ccc(OC)cc1] | 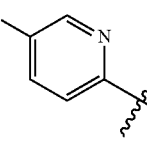 |
| 45 | 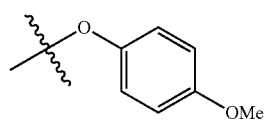 | 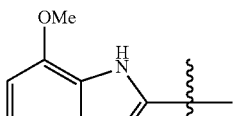 |

TABLE 1-continued
Additional Compounds
| Cmpd. No. | —W—R¹ | R² |
|---|---|---|
| 46 | 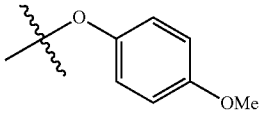 [SMILES: *Oc1ccc(OC)cc1] | 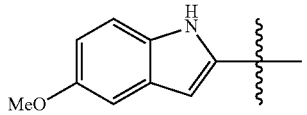 [SMILES: *c1cc2cc(OC)ccc2[nH]1] |
| 47 | 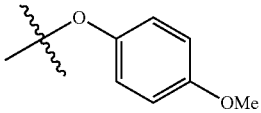 | 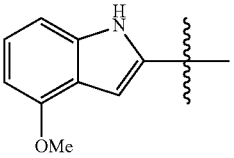 [SMILES: *c1cc2c(OC)cccc2[nH]1] |
| 48 | 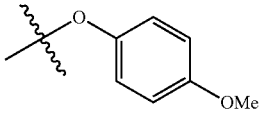 [SMILES: *Oc1ccc(OC)cc1] | 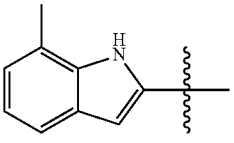 [SMILES: *c1cc2cccc(C)c2[nH]1] |
| 49 | 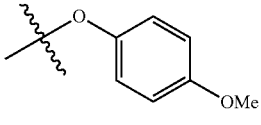 | 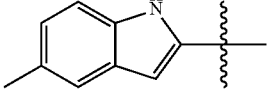 |
| 50 | 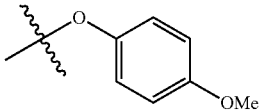 [SMILES: *Oc1ccc(OC)cc1] | 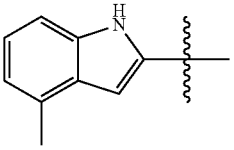 [SMILES: *c1cc2c(C)cccc2[nH]1] |
| 51 | 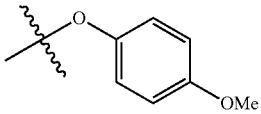 [SMILES: *Oc1ccc(OC)cc1] | 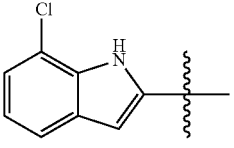 [SMILES: *c1cc2cccc(Cl)c2[nH]1] |
| 52 | 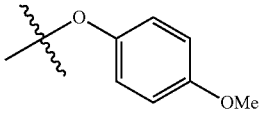 [SMILES: *Oc1ccc(OC)cc1] | 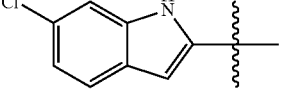 |
| 53 | 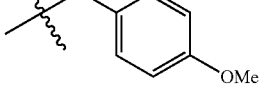 | 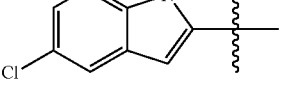 |
| 54 | 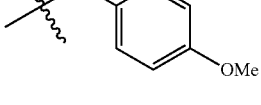 | 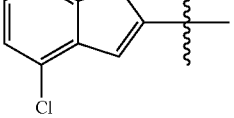 |
| 55 | 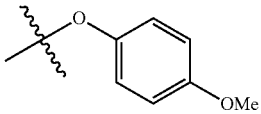 [SMILES: *Oc1ccc(OC)cc1] | 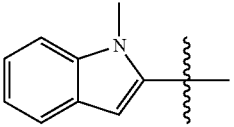 [SMILES: *c1cc2ccccc2n1C] |

TABLE 1-continued

Additional Compounds

| Cmpd. No. | —W—R¹ | R² |
|---|---|---|
| 56 | 4-MeO-phenoxy | 1H-pyrrolo[2,3-b]pyridin-2-yl |
| 57 | 4-MeO-phenoxy | 1H-pyrrolo[2,3-c]pyridin-2-yl |
| 58 | 4-MeO-phenoxy | 1H-pyrrolo[3,2-c]pyridin-2-yl |
| 59 | 4-MeO-phenoxy | 1H-pyrrolo[3,2-b]pyridin-2-yl |
| 60 | 4-MeO-phenoxy | 1H-benzimidazol-2-yl |
| 61 | 4-MeO-phenoxy | benzothiophen-2-yl |
| 62 | 4-MeO-phenoxy | benzofuran-2-yl |
| 63 | 4-MeO-phenoxy | cyclohexyl |
| 64 | 4-MeO-phenoxy | —CH₃ |
| 65 | 4-MeO-phenoxy | 4-MeO-phenyl |
| 66 | benzo[d][1,3]dioxol-5-yloxy | 3,4-di-MeO-phenyl |

TABLE 1-continued
Additional Compounds
| Cmpd. No. | —W—R¹ | R² |
|---|---|---|
| 67 | 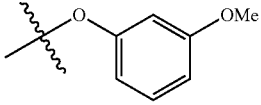 [SMILES: *Oc1cccc(OC)c1] | 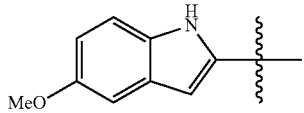 [SMILES: *c1cc2cc(OC)ccc2[nH]1] |
| 68 | 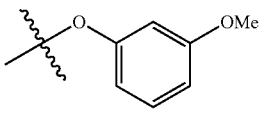 [SMILES: *Oc1cccc(OC)c1] | 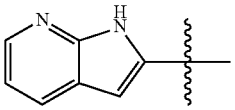 [SMILES: *c1cc2cccnc2[nH]1] |
| 70 | 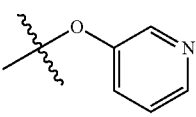 [SMILES: *Oc1cccnc1] | 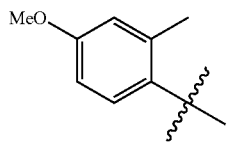 |
| 71 | 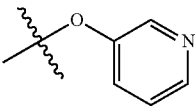 [SMILES: *Oc1cccnc1] | 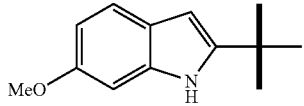 |
| 72 | 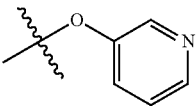 [SMILES: *Oc1cccnc1] | 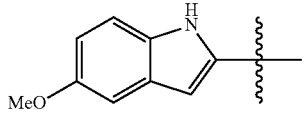 [SMILES: *c1cc2cc(OC)ccc2[nH]1] |
| 73 | 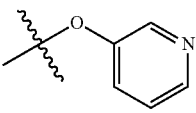 [SMILES: *Oc1cccnc1] | 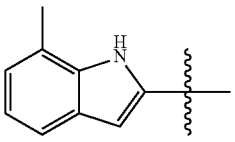 [SMILES: *c1cc2cccc(C)c2[nH]1] |
| 74 | 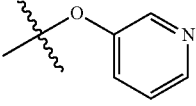 | 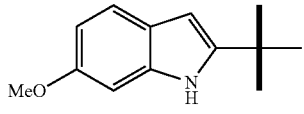 |
| 75 | 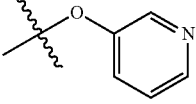 [SMILES: *Oc1cccnc1] | 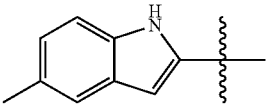 [SMILES: *c1cc2cc(C)ccc2[nH]1] |
| 76 | 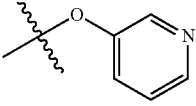 [SMILES: *Oc1cccnc1] | 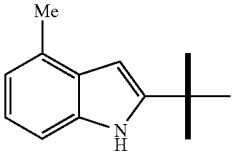 |
| 77 | 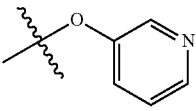 [SMILES: *Oc1cccnc1] | 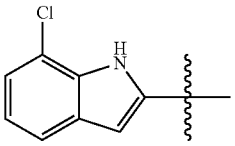 [SMILES: *c1cc2cccc(Cl)c2[nH]1] |
| 78 | 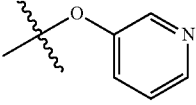 | 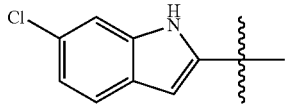 [SMILES: *c1cc2ccc(Cl)cc2[nH]1] |

TABLE 1-continued

Additional Compounds

| Cmpd. No. | —W—R¹ | R² |
|---|---|---|
| 79 | 3-pyridyloxy | 5-chloro-1H-indol-2-yl |
| 80 | 3-pyridyloxy | 4-chloro-1H-indol-2-yl |
| 81 | 3-pyridyloxy | 1-methyl-1H-indol-2-yl |
| 82 | 3-pyridyloxy | 1-methyl-1H-indol-3-yl |
| 83 | 3-pyridyloxy | 1H-pyrrolo[2,3-b]pyridin-2-yl |
| 85 | 3-pyridyloxy | 1H-pyrrolo[3,2-c]pyridin-2-yl |
| 88 | 3-pyridyloxy | benzofuran-2-yl |
| 90 | 3-pyridyloxy | 1H-pyrrol-2-yl |
| 92 | 3-methoxyphenoxy | 1H-indol-2-yl |
| 93 | 3-(methylthio)phenoxy | 1H-indol-2-yl |
| 94 | 3-methoxyphenoxy | 1H-indol-2-yl |

TABLE 1-continued
Additional Compounds
| Cmpd. No. | —W—R¹ | R² |
|---|---|---|
| 95 | 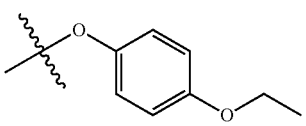 [SMILES: *Oc1ccc(OCC)cc1] | 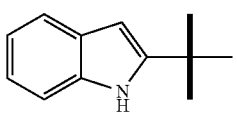 |
| 96 | 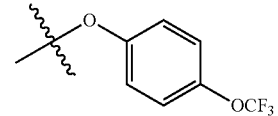 [SMILES: *Oc1ccc(OC(F)(F)F)cc1] | 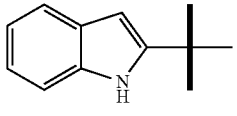 |
| 97 | 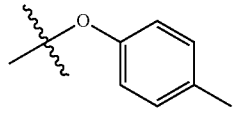 [SMILES: *Oc1ccc(C)cc1] | 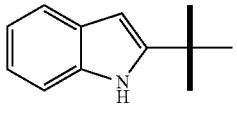 |
| 98 | 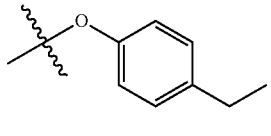 [SMILES: *Oc1ccc(CC)cc1] | 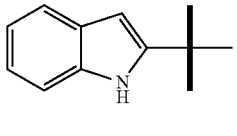 |
| 99 | 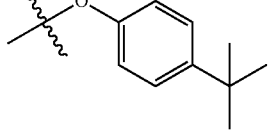 | 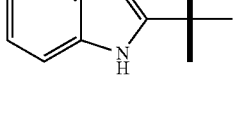 |
| 100 | 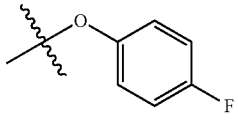 [SMILES: *Oc1ccc(F)cc1] | 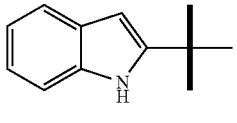 |
| 101 | 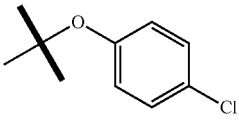 | 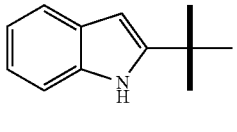 |
| 102 | 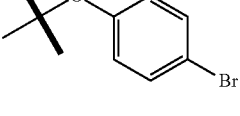 | 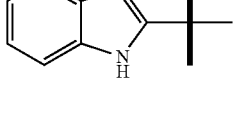 |
| 103 | 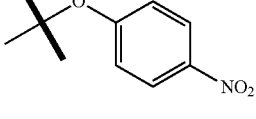 | 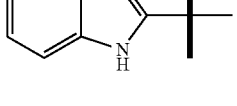 |
| 104 | 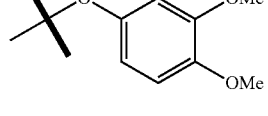 | 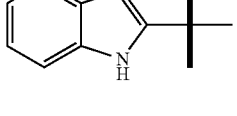 |
| 105 | 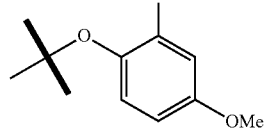 | 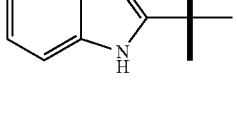 |

TABLE 1-continued

Additional Compounds

| Cmpd. No. | —W—R¹ | R² |
|---|---|---|
| 106 | 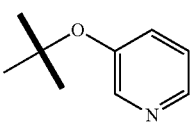 | 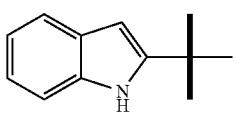 |
| 107 | 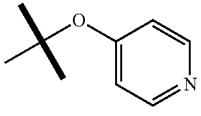 | 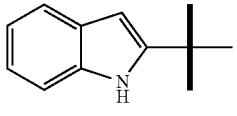 |
| 108 | 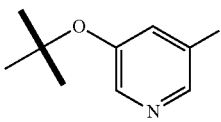 | 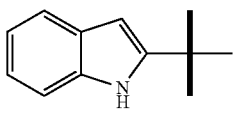 |
| 109 | 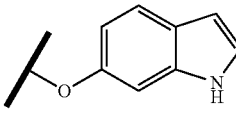 | 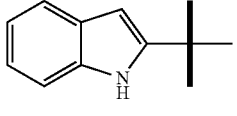 |

The following compounds are also made by the methods used to prepare Compound 1. Those of skill in the art will recognize the routine changes to the procedure for preparing Compound 1 needed to produce the following compounds. Starting material for certain of the compounds in the "additional compounds" table can also be made by the following general schemes. For example starting material for compound 118 can be made by Scheme A and starting material for compounds 120-121 can be made by Scheme B.

Scheme A

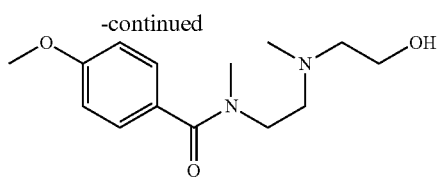

Scheme B

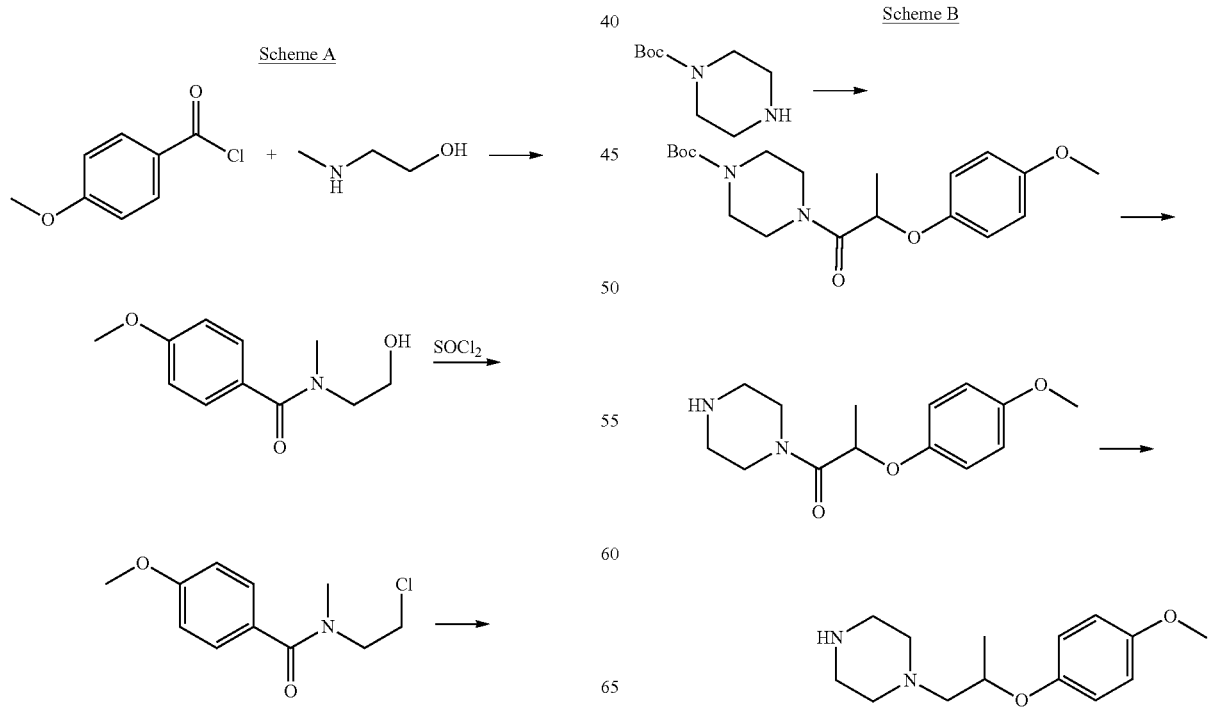

| Cmpd. No. | Structure |
|---|---|
| | Additional compounds (Table, 1 continued) |
| 111 | 4-MeO-C6H4-C(O)-N(piperazine)N-CH(CH3)-CH2-O-C6H4-4-OMe |
| 112 | 4-MeO-C6H4-C(O)-N(piperazine)N-(CH2)3-O-C6H4-4-OMe |
| 113 | 4-MeO-C6H4-C(O)-N(piperazine)N-(CH2)3-C6H4-4-OMe |
| 114 | 4-MeO-C6H4-C(O)-N(piperazine)N-C6H4-4-OMe |
| 115 | 4-Cl-C6H4-C(O)-N(piperazine)N-(CH2)3-O-C6H4-4-OMe |
| 116 | 4-MeO-C6H4-S(O)2-N(piperazine)N-(CH2)2-O-C6H4-4-OMe |
| 117 | 4-MeO-C6H4-C(O)-N(piperidine, 4-yl)-(CH2)2-O-C6H4-4-OMe |
| 118 | 4-MeO-C6H4-C(O)-N(Me)-(CH2)2-N(Me)-(CH2)2-O-C6H4-4-OMe |

-continued

| Additional compounds (Table, 1 continued) |
| --- |

| Cmpd. No. | Structure |
| --- | --- |
| 119 | indole-2-C(O)-piperazine-CH2CH2-N(Me)-C6H4-OMe |
| 120 | indole-2-C(O)-piperazine-CH2CH(Me)-O-C6H4-OMe |
| 121 | indole-2-C(O)-piperazine-CH2CH(Me)-O-C6H4-Cl |
| 122 | indole-2-C(O)-piperazine-(CH2)3-O-C6H4-OMe |
| 123 | indole-2-C(O)-piperazine-(CH2)4-O-C6H4-OMe |
| 124 | indole-2-C(O)-piperidine-4-CH2CH2-O-C6H4-OMe |
| 125 | indole-2-C(O)-CH2-piperazine-CH2CH2-O-C6H4-OMe |

Analytical Data for Select Compounds (4-(2-(pyridin-3-yloxy)ethyl)piperazin-1-yl)(1H-pyrrolo[2,3-b]pyridin-2-yl)methanone (Compound 4)

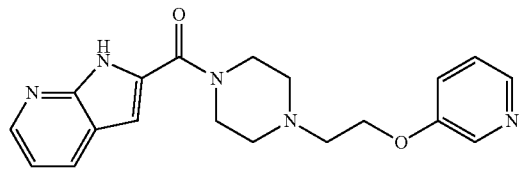 [SMILES: O=C(c1cc2cccnc2[nH]1)N1CCN(CCOc2cccnc2)CC1]

$^1$H NMR (500 MHz, CDCl$_3$) δ 2.66-2.78 (m, 4H), 2.90 (t, J=5.5 Hz, 2H), 3.97 (s, 4H), 4.19 (t, J=5.5 Hz, 2H), 6.73 (d, J=1.5 Hz, 1H), 7.14 (dd, J=7.9, 4.7 Hz, 1H), 7.19-7.26 (m, 2H), 7.99 (dd, J=7.9, 1.4 Hz, 1H), 8.24 (dd, J=4.0, 2.0 Hz, 1H), 8.34 (dd, J=2.4, 1.0 Hz, 1H), 8.51 (dd, J=4.7, 1.5 Hz, 1H), 10.81 (s, 1H). $^{13}$C NMR (125 MHz, CDCl$_3$) δ 41.00, 53.62, 57.02, 66.25, 103.40, 116.87, 119.80, 121.27, 123.87, 129.86, 130.36, 137.99, 142.44, 145.98, 147.71, 154.81, 162.04. HRMS (m/z): calcd. for $C_{19}H_{22}N_5O_2$ [M+H]$^+$ 352.1773; found 352.1769; HPLC purity: 100%; FTIR (neat): 3055, 2942, 2812, 1615, 1574, 1428, 1225 cm$^{-1}$.

6-methoxy-1H-indol-2-yl)(4-(2-(4-methoxyphenoxy)ethyl)piperazin-1-yl)methanone: (Compound 32)

(32)

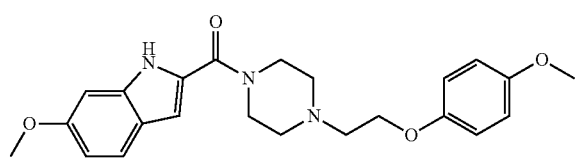

$^1$H NMR (500 MHz, CDCl$_3$) δ 2.63-2.72 (m, 4H), 2.84 (t, J=5.6 Hz, 2H), 3.77 (s, 3H), 3.86 (s, 3H), 3.93 (d, J=20.2 Hz, 4H), 4.09 (t, J=5.6 Hz, 2H), 6.72 (dd, J=2.1, 0.7 Hz, 1H), 6.77-6.90 (m, 6H), 7.50 (d, J=8.8 Hz, 1H), 9.10 (s, 1H). $^{13}$C NMR (125 MHz, CDCl$_3$) δ 0.00, 53.60, 55.52, 55.73, 57.28, 66.52, 76.76, 77.02, 77.27, 93.69, 105.63, 111.91, 114.65, 115.59, 121.81, 122.66, 128.13, 136.51, 152.77, 153.98, 158.22, 162.18; HRMS (m/z): calcd. for $C_{23}H_{28}N_3O_4$ [M+H]$^+$ 410.2080; found 410.2074; HPLC purity: 99.5%; FTIR (neat): 3265, 2937, 1596, 1505, 1231 cm$^{-1}$.

Example 3. D$_3$ DAR Beta-Arrestin Recruitment Assay

A D$_3$ DAR β-arrestin cell line from DiscoverX (Fremont, CA) was used as described in the protocol below (Table 2) for the screen. A CHO cell line engineered to overexpress the D$_3$ DAR fused with a small 42-amino acid fragment of β-galactosidase called ProLink™ and a fusion protein consisting of 3-arrestin and a larger N-terminal deletion mutant of β-galactosidase was used (DiscoverX catalogue number 93-0579C$_2$). When the D$_3$ DAR is activated by dopamine, it stimulates binding of β-arrestin to ProLink-tagged D$_3$ DARs, and the two complementary parts of β-galactosidase form a functional enzyme. When substrate (PathHunter® Detection reagent, DiscoverX 93-0001) is added, β-galactosidase hydrolyzes it and generates a chemiluminescent signal.

TABLE 2

Protocol for D$_3$ DAR β-arrestin recruitment assay

| Sequence | Parameter | Value | Description |
|---|---|---|---|
| 1 | Cells | 3 μL | 2,100 cells/well |
| 2 | Time | 16-20 hr | Incubate at 37° C. and 5% CO$_2$ |
| 3 | Reagent | 23 nL | Compound library, dopamine as control (in DMSO) |
| 4 | Time | 90 min | Incubate at 37° C. and 5% CO$_2$ |
| 5 | Detection Reagent | 1.5 μL | 1:5:19 Galacton Star Substrate:Emerald II solution:PathHunter buffer |
| 6 | Time | 60 min | Room temperature incubation |
| 7 | Detector | 30 sec | Luminescent settings. ViewLux plate reader |

Example 4. D$_2$ DAR Beta-Arrestin Recruitment Assay

For a secondary-screen and selectivity assays, DAR PathHunter® β-arrestin GPCR cell lines from DiscoverX (Fremont, CA) were used. In the D$_2$ Receptor PathHunter® β-arrestin GPCR cell line, the D$_2$ DAR is overexpressed and fused with a small 42-amino acid fragment of β-galactosidase called ProLink™ on a CHO cellular background expressing a fusion protein of β-arrestin and a larger N-terminal deletion mutant of β-galactosidase ("enzyme acceptor"). When DAR is activated by dopamine, it stimulates binding of β-arrestin to the ProLink-tagged DAR and the two complementary parts of β-galactosidase form a functional enzyme. When substrate (PathHunter™ Detection reagent) is added, β-galactosidase hydrolyzes it and generates a chemiluminescent signal. Table 3 summarizes the protocol for the D$_2$ DAR β-arrestin recruitment assay.

TABLE 3

Protocol for the D$_2$ DAR β-arrestin recruitment assay

| Sequence | Parameter | Value | Description |
|---|---|---|---|
| 1 | Cells | 3 μL | 2.100 cells/well |
| 2 | Time | 16-20 hr | Incubate at 37° C. and 5% CO$_2$ |
| 3 | Reagent | 23 nL | Compound library, dopamine as control (in DMSO) |
| 4 | Time | 90 min | Incubate at 37° C. and 5% CO$_2$ |
| 5 | Detection Reagent | 1.5 μL | 1:5:19 Galacton Star Substrate:Emerald II solution:PathHunter buffer |
| 6 | Time | 60 min | Room temperature incubation |
| 7 | Detector | 30 sec | Luminescent settings, ViewLux plate reader |

Table 4 shows the D$_3$ agonist, D$_2$ agonist, and D$_2$ antagonist activity of compounds 1-32 in the beta-arrestin recruitment assays of Examples 3-4.

TABLE 4

| Cmpd. No. | $D_3$ $EC_{50}$ (nM) | $D_3$ $E_{max}$ | $D_2$ $EC_{50}$ (nM) | $D_2$ $E_{max}$ | $D_2$ $IC_{50}$ (nM) | $D_2$ $I_{max}$ |
|---|---|---|---|---|---|---|
| 1 | 36 | 106 | >10,000 | Curve Interrupted | >50000 | Curve Interrupted |
| 2 | 9.2 | 83 | 1800 | 49 | 535 | 37 |
| 3 | 11.5 | 95 | 1000 | 75 | None | None |
| 4 | 13.5 | 99 | 210 | 99 | None | None |
| 5 | 33 | 112 | 2400 | 61 | None | None |
| 6 | 13.3 | 102 | 617 | 34 | 2100 | 60 |
| 7 | 45 | 98 | 4100 | 71 | None | None |
| 8 | 81 | 117 | 780 | 66 | None | None |
| 9 | 285 | 120 | 660 | 29 | 2000 | 53 |
| 10 | 42 | 105 | 1700 | 57 | None | None |
| 11 | 50 | 129 | 128 | 76 | None | None |
| 12 | 63 | 108 | 1800 | 61 | None | None |
| 13 | 5.0 | 79 | 790 | 56 | None | None |
| 14 | 33.8 | 105 | 2300 | 48 | >100000 | Curve interrupted |
| 15 | 126 | 90 | >50,000 | Curve interrupted | 9700 | 72 |
| 16 | 60.9 | 84 | None | None | 440 | 100 |
| 17 | 3.0 | 96 | 183 | 89 | None | None |
| 18 | 4.4 | 107 | 217 | 82 | None | None |
| 19 | 98 | 119 | 1400 | 90 | None | None |
| 20 | 4.3 | 106 | 138 | 74 | None | None |
| 21 | 33 | 127 | 617 | 74 | None | None |
| 22 | 9.5 | 94 | 4400 | 91 | None | None |
| 23 | 6.4 | 107 | 364 | 81 | None | None |
| 24 | 6.9 | 97 | 180 | 70 | None | None |
| 25 | 13 | 113 | 1300 | 101 | None | None |
| 26 | 25.7 | 108 | 786 | 81 | None | None |
| 27 | 37.6 | 112 | 6200 | 53 | None | None |
| 28 | 59 | 97 | 2600 | 97 | None | None |
| 29 | 284 | 110 | 1700 | 67 | None | None |
| 30 | 266 | 106 | 4300 | 37 | 744 | 30 |
| 31 | 208 | 112 | 2500 | 19 | 4600 | 64 |
| 32 | 155 | 91 | 5200 | 62 | None | None |
| 33 | 710 | 104 | none | none | 14,000 | 100 |
| 34 | 278 | 36 | none | none | 9,000 | 99 |
| 35 | 2,600 | 44 | none | none | >50,000 | curve interrupted |
| 36 | 1,000 | 103 | none | none | >10,000 | 101 |
| 37 | none | none | none | none | >50,000 | 100 |
| 38 | 3,500 | 50 | none | none | >100,000 | curve interrupted |
| 39 | 310 | 78 | none | none | >10,000 | 87 |
| 40 | 17 | 123 | 2,900 | 96 | >100,000 | curve interrupted |
| 41 | 548 | 70 | none | none | >50,000 | 100 |
| 42 | 2,500 | 121 | none | none | >100,000 | curve interrupted |
| 43 | 22,000 | 50 | none | none | none | none |
| 44 | 2,100 | 97 | >50,000 | curve interrupted | >100,000 | curve interrupted |
| 45 | 980 | 115 | 6,000 | 56 | >100,000 | curve interrupted |
| 46 | 520 | 109 | 7,800 | 46 | >100,000 | curve interrupted |
| 47 | 411 | 116 | 5,200 | 33 | >100,000 | curve interrupted |
| 48 | 473 | 103 | 10,100 | 49 | >100,000 | curve interrupted |
| 49 | 611 | 119 | >50,000 | curve interrupted | >100,000 | curve interrupted |
| 50 | 266 | 106 | 4,300 | 37 | 744 | 30 |
| 51 | 563 | 122 | 13,000 | 70 | >100,000 | curve interrupted |
| 52 | 225 | 130 | 3,500 | 58 | >100,000 | curve interrupted |
| 53 | 2,900 | 117 | none | none | none | none |
| 54 | 160 | 122 | 7,100 | 57 | >100,000 | curve interrupted |
| 55 | 617 | 96 | none | none | 16,000 | 99 |
| 56 | 167 | 122 | 413 | 94 | none | none |
| 57 | 810 | 105 | 7,800 | 21 | >100,000 | curve interrupted |

TABLE 4-continued

Compound Activity

| Cmpd. No. | $D_3$ $EC_{50}$ (nM) | $D_3$ $E_{max}$ | $D_2$ $EC_{50}$ (nM) | $D_2$ $E_{max}$ | $D_2$ $IC_{50}$ (nM) | $D_2$ $I_{max}$ |
|---|---|---|---|---|---|---|
| 58 | 576 | 107 | 5,500 | 28 | >100,000 | curve interrupted |
| 59 | 2,800 | 103 | >100,000 | curve interrupted | none | none |
| 60 | 192 | 95 | none | none | >50,000 | curve interrupted |
| 61 | 3,300 | 51 | none | none | 5,100 | 96 |
| 62 | 430 | 80 | none | none | 7,700 | 100 |
| 63 | >50,000 | curve interrupted | none | none | >50,000 | curve interrupted |
| 64 | 35 | 9,700 | none | none | None | none |
| 65 | none | none | none | none | >50,000 | curve interrupted |
| 66 | 353 | 104 | 7,400 | 54 | None | none |
| 67 | 284 | 110 | 1,700 | 67 | None | none |
| 68 | 50.0 | 129 | 128 | 76 | None | none |
| 70 | 116 | 102 | 4,600 | 52 | >100,000 | curve interrupted |
| 71 | 6.4 | 107 | 364 | 81 | none | none |
| 72 | 59 | 97 | 2,600 | 97 | none | none |
| 73 | 25.7 | 108 | 786 | 81 | none | none |
| 74 | 4.3 | 106 | 138 | 74 | none | none |
| 75 | 13 | 113 | 1,300 | 101 | none | none |
| 76 | 6.9 | 97 | 180 | 70 | none | none |
| 77 | 33 | 127 | 617 | 74 | none | none |
| 78 | 3.0 | 96 | 183 | 89 | none | none |
| 79 | 98 | 119 | 1,400 | 90 | none | none |
| 80 | 4.4 | 107 | 217 | 82 | none | none |
| 81 | 37.6 | 112 | 6,200 | 53 | none | none |
| 82 | 9.5 | 94 | 4,400 | 91 | none | none |
| 83 | 13.5 | 99 | 210 | 99 | none | none |
| 85 | 63 | 108 | 1,800 | 61 | none | none |
| 88 | 42 | 104 | 1,700 | 57 | none | none |
| 90 | 118 | 110 | 6,100 | 34 | >100,000 | curve interrupted |
| 92 | none | none | none | none | >100,000 | curve interrupted |
| 93 | 630 | 89 | none | none | >100,000 | curve interrupted |
| 94 | 33.8 | 105 ± 9.3 | 2,300 | 48 | >100,000 | curve interrupted |
| 95 | >100,000 | curve interrupted | none | none | >100,000 | curve interrupted |
| 96 | 3,800 | 100 | >100,000 | curve interrupted | >100,000 | curve interrupted |
| 97 | 151 | 91 | >50,000 | curve interrupted | >100,000 | curve interrupted |
| 98 | 1,600 | 98 | none | none | >50,000 | curve interrupted |
| 99 | none | none | none | none | >100,000 | curve interrupted |
| 100 | 126 | 90 | >50,000 | curve interrupted | 9,700 ± 5,800 | 72 ± 4.6 |
| 101 | 114 | 118 | none | none | >50,000 | curve interrupted |
| 102 | 105 | 106 | none | none | >100,000 | curve interrupted |
| 103 | 1,300 | 92 | none | none | none | none |
| 104 | 710 | 111 | none | none | >50,000 | curve interrupted |
| 105 | 78 | 123 | >50,000 | curve interrupted | >50,000 | curve interrupted |
| 106 | 8.1 | 103 | 252 | 65 | none | none |
| 107 | 472 | 71 | none | none | >100,000 | curve interrupted |
| 108 | 5.0 | 79 | 790 | 56 | none | none |
| 109 | 60.9 | 84 | none | none | 440 | 100 |
| 111 | 9,300 | 106 | none | none | >100,000 | curve interrupted |
| 112 | none | none | none | none | 6,500 | 97 |
| 113 | none | none | none | none | 6,700 | 96 |
| 114 | none | none | none | none | >100,000 | curve interrupted |
| 115 | none | none | none | none | 9,000 | 107 |

TABLE 4-continued

Compound Activity

| Cmpd. No. | $D_3$ $EC_{50}$ (nM) | $D_3$ $E_{max}$ | $D_2$ $EC_{50}$ (nM) | $D_2$ $E_{max}$ | $D_2$ $IC_{50}$ (nM) | $D_2$ $I_{max}$ |
|---|---|---|---|---|---|---|
| 116 | none | none | >100,000 | curve interrupted | none | none |
| 117 | none | none | none | none | none | none |
| 118 | none | none | none | none | 18,000 | 72 |
| 119 | 1,900 | 45 | none | none | >100,000 | curve interrupted |
| 120 | 82 | 108 | 3,300 | 46 | none | none |
| 121 | 32 | 101 | 1,900 | 43 | none | none |
| 122 | none | none | none | none | 691 | 97 |
| 123 | none | none | none | none | 1200 | 97 |
| 124 | none | none | none | none | none | none |
| 125 | none | none | none | none | none | none |

Example 5. $D_3$ Radioligand Binding Assay

Compounds were tested for their ability to compete with the orthosteric radioligand [$^3$H]methylspiperone for binding to the $D_3$ DAR using stable HEK cell lines expressing the $D_3$ DAR (Codex Biosciences, Gaithersburg, MD, Catalogue no. CB-80300-206) as described in the detailed protocol below presented in Table 5. Cells were cultured in Dulbecco's modified Eagle's Medium (Corning, catalogue no. 10-013) containing 10% FBS, 1,000 units/mL Penicillin, 1,000 mg/mL Streptomycin, 100 mM sodium pyruvate, 1 μg/mL Gentamicin, and 250 mg/mL G418. All cells were maintained at 37° C. in 500 $CO_2$ and 90% humidity. For radioligand binding assays cells were removed mechanically using calcium-free Earle's balanced salt solution (EBSS). Intact cells were collected by centrifugation and then lysed with 5 mM Tris-HCl and 5 mM $Mg_2$ at pH 7.4. Homogenates were centrifuged at 30,000×g for 30 minutes. The membranes were re-suspended in EBSS (US Biological, catalogue no. E0249-05) pH 7.4 to a concentration of 16 μg/mL. For competition binding studies, membrane preparations were incubated for 90 minutes at room temperature with various concentrations of compound and a single concentration of [$^3$H]methylspiperone (Perkin Elmer, NET856) in a reaction volume of 250 BL. Non-specific binding was determined in the presence of 4 μM (+)-butaclamol (Sigma-Aldrich, catalogue no. D033). Bound ligand was separated from unbound by filtration through GF/C filters using a PerkinElmer cell harvester and quantified on a Top-count (PerkinElmer). Ki values were determined using Cheng-Prusoff equation from observed $IC_{50}$ values and ligand Kd values from separate saturation experiments.

TABLE 5

Protocol for the radioligand binding assay

| Sequence | Parameter | Value | Description |
|---|---|---|---|
| 1 | Cells | 25 mL | 2 × 10$^7$ cells/flask |
| 2 | Time | 24 h | Incubate at 37° C. and 5% $CO_2$ |
| 3 | Reagent | 10 mL | EBSS (-) |
| 4 | Time | 10 min | Room Temperature |
| 5 | Centrifuge | 900 × g | Pellet cells |
| 6 | Lysis | 6 mL | Re-suspend and homogenize in lysis buffer |
| 7 | Centrifuge | 30,000 × g | Pellet homogenate |
| 8 | Buffer | 10 mL | Re-suspend in EBSS to 16 μg protein/mL |
| 9 | Reagent | 25 μL | Buffer/Butaclamol/Test compound per assay well |
| 10 | Reagent | 125 μL | Radioligand per assay well |
| 11 | Lysate | 100 μL | Membrane preparation per assay well |
| 12 | Time | 90 min | Incubate at room temperature with shaking |
| 13 | Filter | 4 washes | Filter membranes onto GF/C filter plates |
| 14 | Reagent | 50 μL | Perkin Elmer scintillation cocktail |

Example 6. Orthogonal Screening Assays

Orthogonal testing using an unrelated assay of β-arrestin recruitment, as well as assays of G-protein mediated signaling and assays of ERK phosphorylation also show that compound 1 is a potent and fully efficacious D3R-selective agonist.

BRET arrestin recruitment assay. As an orthogonal test using an unrelated assay of D3R-mediated β-arrestin recruitment, an arrestin BRET assay was conducted. HEK293T cells transiently expressing $D_2$-Rluc8, Arrestin3-mvenus and GRK2, or D3-Rluc8, Arrestin3-mvenus, and GRK3 were harvested with EBSS, plated in 96-well plates in Dulbecco's phosphate-buffered saline (DPBS) and incubated at rt for 45 min. Cells were incubated with 5 μM coelenterazine H (the substrate of Rluc8, Nanolight Technology, Pinetop AZ) for 5 min, then stimulated with the indicated concentrations of either dopamine or a test compound of Formula I for 5 min. BRET signal was determined by quantifying and calculating the ratio of the light emitted by mVenus (525 nm) over that emitted by RLuc8 (485 nm) using a PHERAstar FSX Microplate Reader (BMG Labtech).

$G_O$ BRET activation assay. To determine if a test compound of Formula I displays functional selectivity (the ability to selectively activate one signaling pathway versus another), a $G_O$ BRET activation assay was utilized as described in the protocol below (Table 6). Briefly, HEK293T cells transiently expressing either the D2R or D3R and Gα$_{oA}$-Rluc8, untagged-β$_1$, and mVenus-γ$_2$ were harvested with EBSS-, plated in 96-well white plates at 20,000 cells/well in DPBS and incubated at RT for 45 min. Cells were incubated with 5 μM coelenterazine h (Nanolight Technology, Pinetop, AZ) for 5 min, then stimulated with the indicated concentrations of either dopamine or a test compound of Formula I for 5 min. BRET signal was determined by quantifying and calculating the ratio of the light emitted by mVenus (525 nm) over that emitted by RLuc8 (485 nm) using a PHERAstar FSX Microplate Reader (BMG Labtech).

TABLE 6

Protocol for the $G_0$ BRET activation assay

| Sequence | Parameter | Value | Description |
|---|---|---|---|
| 1 | Cells | 100 μL | 200,000 cells/mL in 96 well plate |
| 2 | Time | 45 min | Incubate at room temperature |
| 3 | Reagent | 50 μL | 25 μM coelenterazine |
| 4 | Time | 5 min | Incubate at room temperature |
| 5 | Reagent | 100 μL | Test compound |
| 6 | Time | 5 min | Incubate at room temperature |
| 7 | Detector | BRET signal | 525 nM/485 nM ratio using PHERAstar FSX Microplate Reader (BMG Labtech) |

ERK1/2 Phosphorylation assay. ERK1/2 phosphorylation was measured using the Alphascreen SureFire Ultra ERK kit (PerkinElmer, Waltham, USA). CHO-K1 DiscoverX cells stably expressing either the D2R or D3R were seeded into 384-well small volume white plates at a density of 40,000 cells/well in serum-free Ham's F12 media overnight. Cells were stimulated with the indicated concentration of test compound for 15 min, followed by cell lysis as specified by manufacture's protocol. The plate was shaken for 10 min at RT, followed by the addition of Surefire activation buffer, Surefire reaction buffer, Alphascreen acceptor beads, and Alphascreen donor beads in ratios specified by the manufacturer. The plate was incubated in the dark for 2 h, then read using a PHERAstar FSX Microplate Reader (BMG Labtech).

Example 7. [35S]GTPγS Binding Assay

A [$^{35}$S]GTPγS (Perkin Elmer NEG030H) binding assay was utilized as described in the protocol below (Table 7). Briefly, cells stably expressing $D_2$ DARs (Codex Biosolutions CB-80300-206) were lysed with 1 mM EDTA, 20 mM HEPES, pH 7.4. Homogenates were centrifuged at 30,000×g for 30 minutes. The membranes were re-suspended in 20 mM HEPES, 10 mM $MgCl_2$, 100 mM NaCl, 3 mM EGTA, 0.2 mM sodium metabisulfite, pH 8.0 containing 50 μM GDP and incubated with dopamine or Compound 1 and [$^{35}$S]GTPγS for 1 hour at 30° C. Basal binding was determined in the presence of 10 μM unlabeled GTPγS and non-specific binding was determined in the presence of 4 μM (+)-butaclamol (Sigma-Aldrich D033). Bound ligand was separated from unbound by filtration through GF/C filters using a PerkinElmer cell harvester and quantified on a Top-count (PerkinElmer). Data are expressed as % maximum dopamine response. Compound 1 was found not to activate the $D_2$ DAR in this assay.

TABLE 7

Protocol for the [$^{35}$S]GTPγS binding assay

| Sequence | Parameter | Value | Description |
|---|---|---|---|
| 1 | Cells | 25 mL | $2 \times 10^7$ cells/150 mm dish |
| 2 | Time | 24 h | Incubate at 37° C. and 5% $CO_2$ |
| 3 | Lysis | 5 mL | Scrape cells and homogenize in lysis buffer |
| 4 | Centrifuge | 30,000 × g | Pellet homogenate |
| 5 | Buffer | 5 mL | Re-suspend in assay buffer to 25 μg protein/mL |
| 6 | Reagent | 30 μL | Unlabeled GTPγS/Butaclamol/Test compound per assay well |
| 7 | Reagent | 10 μL | [$^{35}$S]GTPγS |
| 8 | Reagent | 60 μL | Membrane preparation per assay well |
| 9 | Time | 1 hour | Incubate at 30° C. |
| 10 | Filter | 4 washes | Filter membranes onto GF/C filter plates |
| 11 | Reagent | 50 μL | Perkin Elmer scintillation cocktail |

Example 8. DiscoverX gpcrMAX<sup>SM</sup> GPCR Assay Panel

Figure 3:
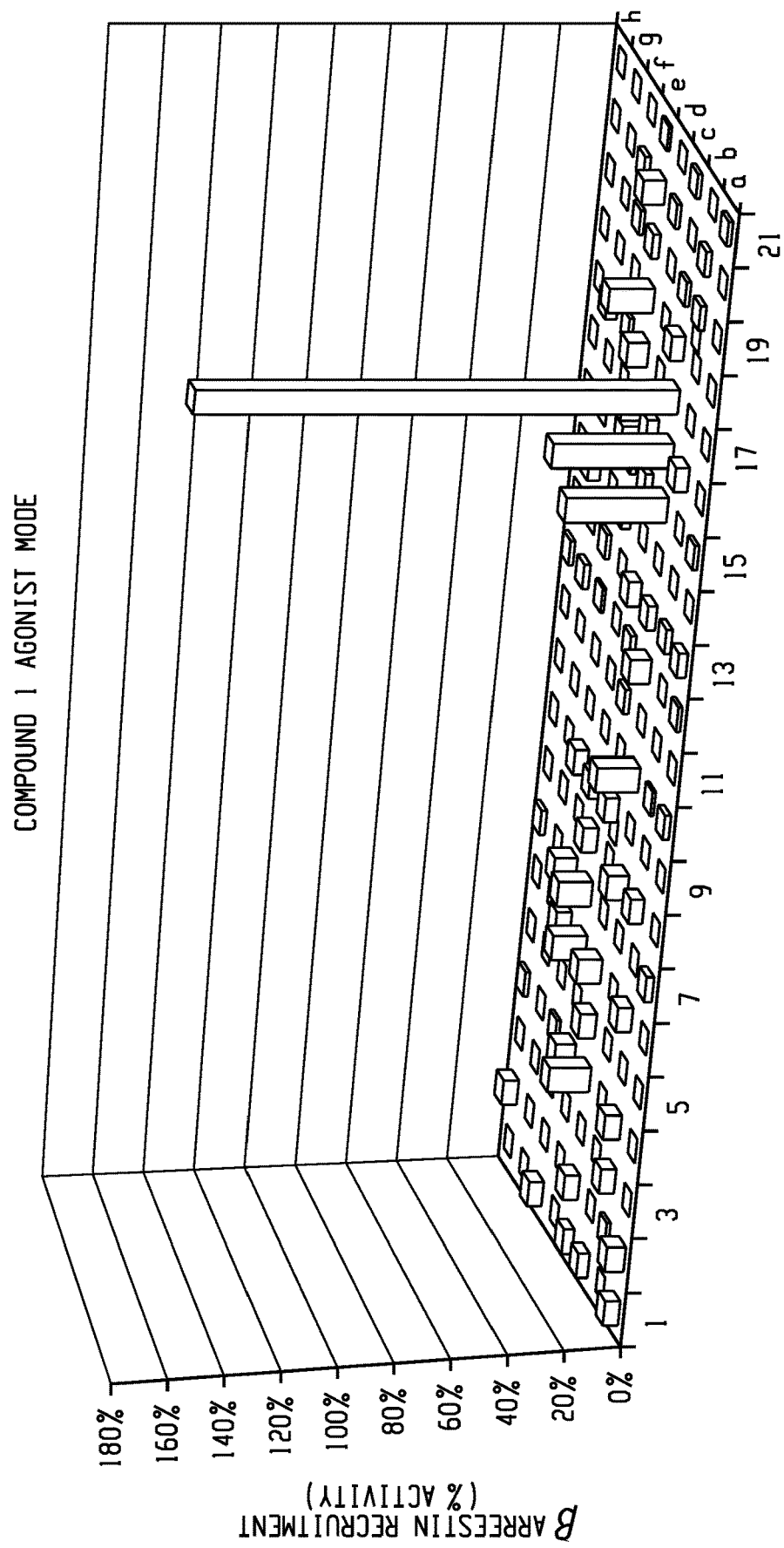
FIG. 3. A 3-dimensional plot of β-arrestin recruitment (% activity) versus receptor type (designated by letter and number), illustrating results of Compound 1 in DiscoverX gpcrMAXSM GPCR assay panel as an agonist.

To determine if a test compound of Formula I displays selectivity for the $D_3$ DAR compared to a large panel of GPCRs, Compound 1 was screened in the DiscoverX gpcrMAX<sup>SM</sup> GPCR Assay Panel of β-arrestin recruitment as an agonist at a single high dose of 10 μM. Methods employed in this study performed at DiscoverX have been adapted from the scientific literature to maximize reliability and reproducibility. Reference standards were run as an integral part of each assay to ensure the validity of the results obtained. Assay results are presented as the mean percent activation of indicated GPCRs (for n=2 replicates) for Compound 1 tested at a concentration of 10 μM. For a full description of the DiscoverX gpcrMAX™GPCR Assay Panel see: http://www.DiscoverX.com. The results are shown numerically in Table 8, and are shown graphically in FIG. 3. In FIG. 3, the grid reference numbers 1-21 and reference letters a-h correspond to the cells of Table 8, with each table cell representing a different GPCR and its recruitment activity in 00. Compound 1 shows a high degree of selectivity among the 168 GPCRs tested.

TABLE 8

β-Arrestin Recruitment activity of Compound 1 with a panel of GPCRs.

| Grid | a | b | c | d | e | f | g | h |
|---|---|---|---|---|---|---|---|---|
| 1 | ADCYA-P1R1 6% | CALCRL RAMP2 −2% | CNR1 5% | EDG3 4% | GLP2R 0% | HTR2C 6% | NPY1R 1% | PTGER3 3% |
| 2 | ADORA3 8% | CALCRL RAMP3 2% | CNR2 −14% | EDG4 6% | GPR1 1% | HTR5A 3% | NPY2R 1% | PTGER4 6% |

TABLE 8-continued

β-Arrestin Recruitment activity of Compound 1 with a panel of GPCRs.

| Grid | a | b | c | d | e | f | g | h |
|---|---|---|---|---|---|---|---|---|
| 3 | ADRA1B 2% | CALCR RAMP2 5% | CRHR1 1% | EDG5 1% | GPR103 −9% | KISS1R 1% | NTSR1 1% | PTGFR 1% |
| 4 | ADRA2A −1% | CALCR RAMP3 6% | CRHR2 0% | EDG6 17% | GPR-109A 10% | LHCGR 2% | OPRD1 1% | PTGIR 4% |
| 5 | ADRA2B −4% | CCKAR 0% | CRTH2 −2% | EDG7 6% | GPR109B 1% | LTB4R 1% | OPRK1 −1% | PTHR1 0% |
| 6 | ADRA2C 1% | CCKBR 4% | CX3CR1 0% | EDG8 10% | GPR119 16% | MC1R 5% | OPRL1 2% | PTHR2 1% |
| 7 | ADRB1 3% | CCR10 −1% | CXCR1 1% | EDNRA 0% | GPR120 12% | MC3R 10% | OPRM1 0% | RXFP3 5% |
| 8 | ADRB2 1% | CCR2 4% | CXCR2 6% | EDNRB 1% | GPR35 6% | MC4R −1% | OXER1 −1% | SCTR 2% |
| 9 | AGTR1 1% | CCR3 1% | CXCR3 5% | F2R 5% | GPR92 6% | MC5R 5% | OXTR 0% | SSTR1 0% |
| 10 | AGTRL1 4% | CCR4 2% | CXCR4 17% | F2RL1 1% | GRPR 0% | MCHR1 1% | P2RY1 1% | SSTR2 0% |
| 11 | AVPR1A 1% | CCR5 0% | CXCR5 1% | F2RL3 4% | HCRTR1 0% | MCHR2 1% | P2RY11 2% | SSTR3 1% |
| 12 | AVPR1B 2% | CCR6 0% | CXCR6 8% | FFAR1 4% | HCRTR2 0% | MLNR 2% | P2RY12 4% | SSTR5 3% |
| 13 | AVPR2 4% | CCR7 4% | CXCR7 3% | FPR1 5% | HRH1 0% | MRGPRX1 3% | P2RY2 1% | TACR1 1% |
| 14 | BDKRB1 0% | CCR8 0% | DRD1 0% | FPRL1 1% | HRH2 3% | MRGPRX2 5% | P2RY4 13% | TACR2 3% |
| 15 | BDKRB2 2% | CCR9 1% | DRD2L 37% | FSHR 5% | HRH3 3% | MTNR1A 2% | P2RY6 6% | TACR3 1% |
| 16 | BRS3 2% | CHRM1 5% | DRD2S 43% | GALR1 4% | HRH4 8% | NMBR 1% | PPYR1 2% | TBXA2R 0% |
| 17 | C3AR1 0% | CHRM2 1% | DRD3 164% | GALR2 1% | HTR1A 8% | NMU1R 2% | PRLHR 4% | TRHR 1% |
| 18 | C5AR1 0% | CHRM3 0% | DRD4 4% | GCGR 1% | HTR1B 16% | NPBWR1 2% | PROKR1 1% | TSHR(L) −1% |
| 19 | C5L2 6% | CHRM4 3% | DRD5 2% | GHSR −3% | HTR1E 4% | NPBWR2 3% | PROKR2 1% | UTR2 0% |
| 20 | CALCR 0% | CHRM5 3% | EBI2 3% | GIPR 3% | HTR1F 10% | NPFFR1 4% | PTAFR 1% | VIPR1 0% |
| 21 | CALCRL RAMP1 2% | CMKLR1 0% | EDG1 2% | GLP1R 1% | HTR2A 4% | NPSR1B 1% | PTGER2 −3% | VIPR2 1% |

The GPCR is listed in text, the activity in %. Grid reference with number and letter is for reference to FIG. 3.

Example 9. Inhibition Binding Profile

Figures 4A, 4B, 4C:
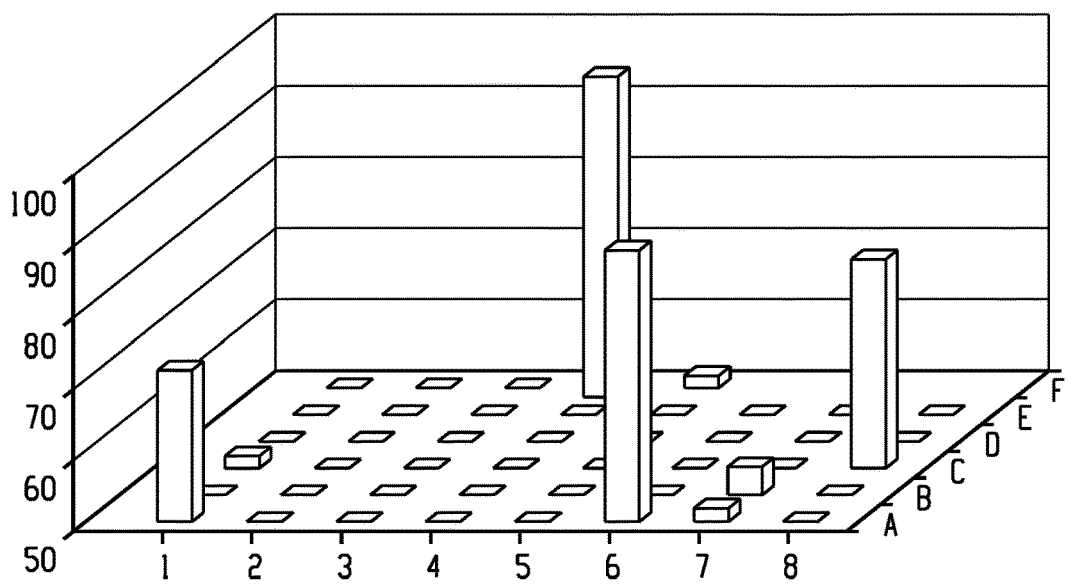
FIG. 4A to FIG. 4C. Inhibition binding profiles of Compound 1, where

Compound 1 displays limited liability for off-target effects as shown by its inhibition binding profiles. Compound 1 was evaluated for binding affinity in the comprehensive panel offered by the Psychoactive Drug Screening Program (PDSP) at the University of North Carolina, Chapel Hill. Experimental conditions will be readily apparent to those of skill in the art. Experimental details, including radioligands used and associated Kd values for each individual target, are listed on the PDSP website http://pdsp.med.unc.edu/. Data represent mean % inhibition (n=4) for each compound binding to various receptor subtypes and ion channels: >50% inhibition is considered significant. The default concentration for primary binding experiments is 10 µM. Ki determinations and full receptor binding profiles were performed for those targets that showed significant inhibition in the primary binding experiments (See Table 9). This screen employs radioligand binding assays for a number of receptors, transporters and some ion channels. FIG. 4A provides the legend of GPCRs tested in this panel. Full numerical results of the panel are shown in FIG. 4B. The histogram of FIG. 4C of the initial screen results show that Compound 1 displays affinity for only the D3R, 5-HT1A, 5-HT2B, and Sigmal receptor. Since the PDSP binding panel showed affinity of Compound 1 at the potentially clinically problematic 5HT2B receptor, and the DiscoverX functional screen lacked the 5HT2B, we tested Compound 1 as both an agonist and antagonist in an HTRF IP1 accumulation assay using a single high concentration of 10 µM using the Eurofins Cerep service. No agonist activity was found, but this dose produced an 80% inhibition of a response elicited by a 30 nM concentration of serotonin (data not shown); indicating that Compound 1 is not an agonist of the 5HT2B, although it may be a low affinity antagonist.

TABLE 9

| | Compound | |
|---|---|---|
| Receptor | Pramipexole | Compound 1 |
| 5HT1A | 6514 | 2108 |
| 5HT1B | 3508 | N/A[b] |
| 5HT1D | >10,000 | N/A[b] |
| 5HT1E | >10,000 | N/A[b] |
| 5HT2A | N/A[b] | N/A[b] |
| 5HT2B | N/A[b] | 674 |
| 5HT2C | N/A[b] | 5997 |
| 5HT3 | >10,000 | N/A[b] |
| 5HT5A | >10,000 | N/A[b] |
| 5HT6 | >10,000 | N/A[b] |
| 5HT7 | 1188 | N/A[b] |
| Alpha1A | >10,000 | N/A[b] |

TABLE 9-continued

| | Compound | |
|---|---|---|
| Receptor | Pramipexole | Compound 1 |
| Alpha1B | N/A$^b$ | N/A$^b$ |
| Alpha1D | N/A$^b$ | N/A$^b$ |
| Alpha2A | 75.7 | >10,000 |
| Alpha2B | 67.7 | N/A$^b$ |
| Alpha2C | 52.2 | 2841 |
| Beta1 | N/A$^b$ | 77 |
| Beta2 | >10,000 | N/A$^b$ |
| Beta3 | >10,000 | N/A$^b$ |
| Bzp site | N/D$^c$ | N/A$^b$ |
| D1 | >10,000 | N/A$^b$ |
| D2 | 743.7 | N/A$^b$ |
| D3 | 0.9 | 1240 |
| D4 | 29 | N/A$^b$ |
| D5 | >10,000 | N/A$^b$ |
| DAT | N/A$^b$ | N/A$^b$ |
| DOR | >10,000 | N/A$^b$ |
| GABAA | N/D$^c$ | N/A$^b$ |
| H1 | N/A$^b$ | N/A$^b$ |
| H2 | 2683 | N/A$^b$ |
| H3 | N/A$^b$ | N/A$^b$ |
| H4 | >10,000 | N/A$^b$ |
| KOR | N/A$^b$ | N/A$^b$ |
| M1 | >10,000 | N/A$^b$ |
| M2 | >10,000 | N/A$^b$ |
| M3 | >10,000 | N/A$^b$ |
| M4 | N/A$^b$ | N/A$^b$ |
| M5 | N/A$^b$ | N/A$^b$ |
| MOR | N/A$^b$ | N/A$^b$ |
| NET | N/A$^b$ | N/A$^b$ |
| PBR | N/D$^c$ | N/A$^b$ |
| SERT | N/A$^b$ | N/A$^b$ |
| Sigma1 | 4446 | 383 |
| Sigma2 | N/A$^b$ | 2750 |

N/A$^b$ indicates no significant bindind affinity was found in the primary assay.
N/D$^c$ indicates the value was not determined.

The results of this binding panel show that Compound 1 is a highly selective compound as assessed by the PDSP, cross reacting with relatively few other GPCR orthosteric sites, and even then, only at concentrations higher than needed to fully active the D3R. It is more selective than the clinically used D3R-preferring agonist pramipexole.

Example 10. Mutagenesis Studies

Figure 5:
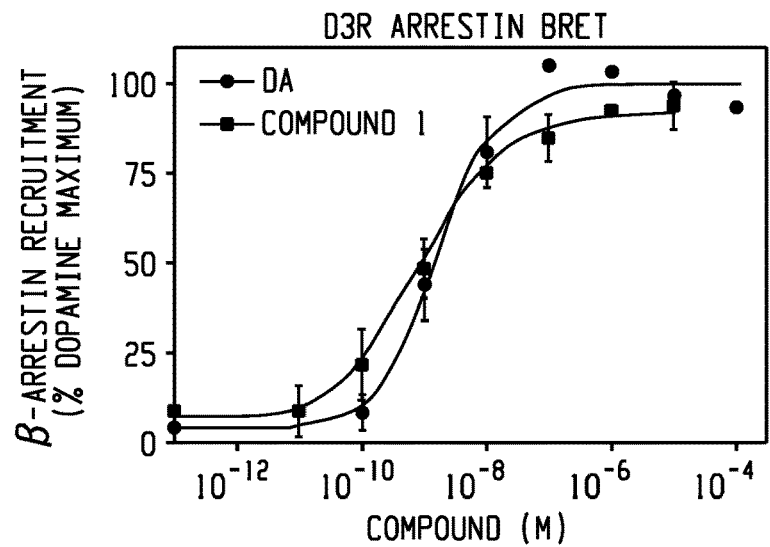
FIG. 5. Arrestin BRET and Go BRET assays showing the effect of the Y198A and Y365A mutations on Compound 1 and Dopamine potency.
Figure 5:
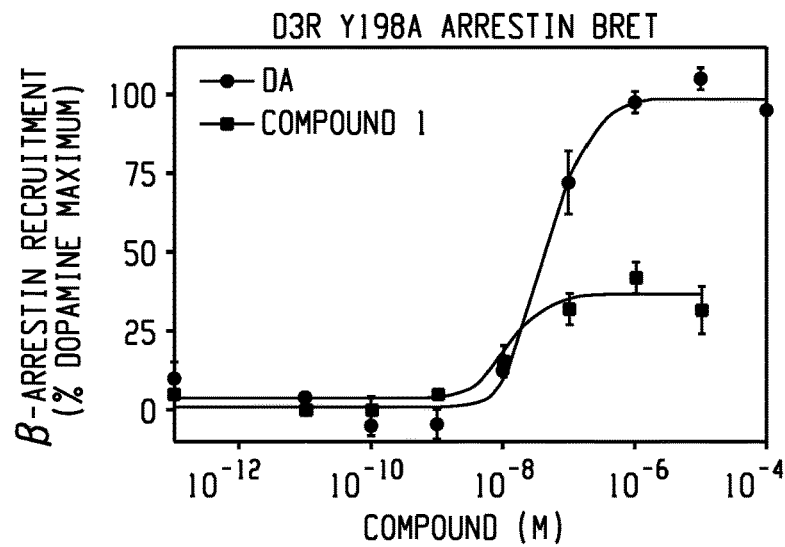
Figure 5:
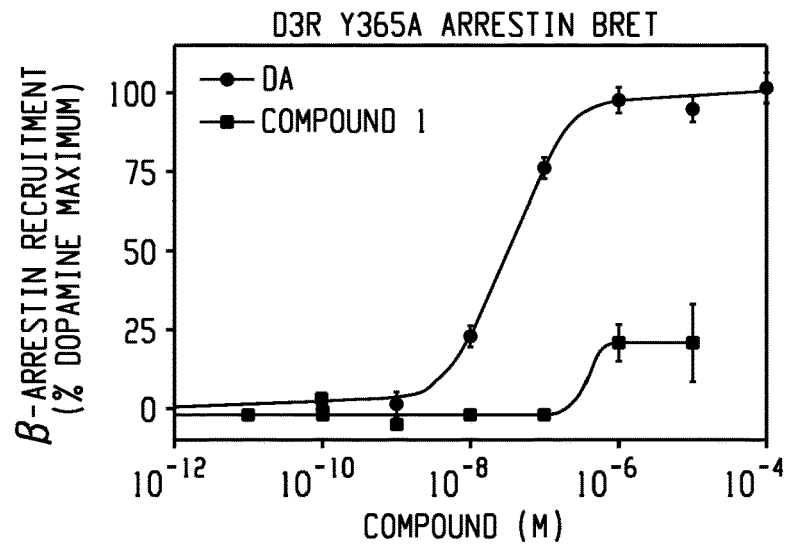
Figure 5:
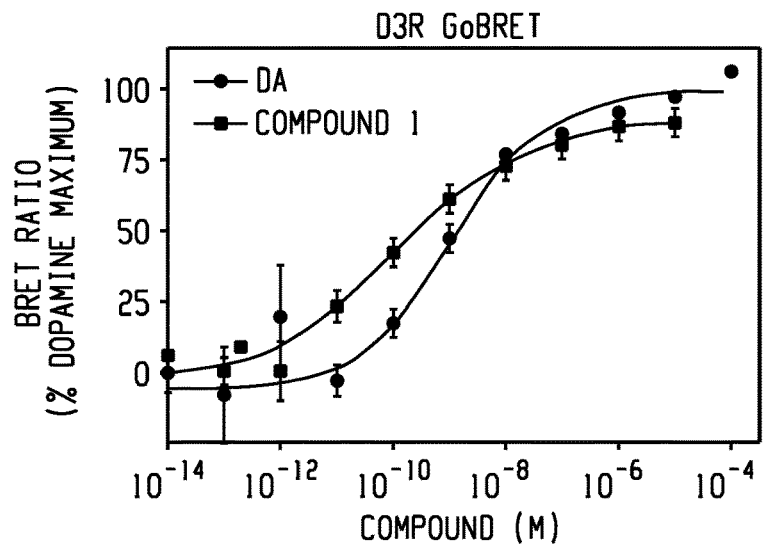
Figure 5:
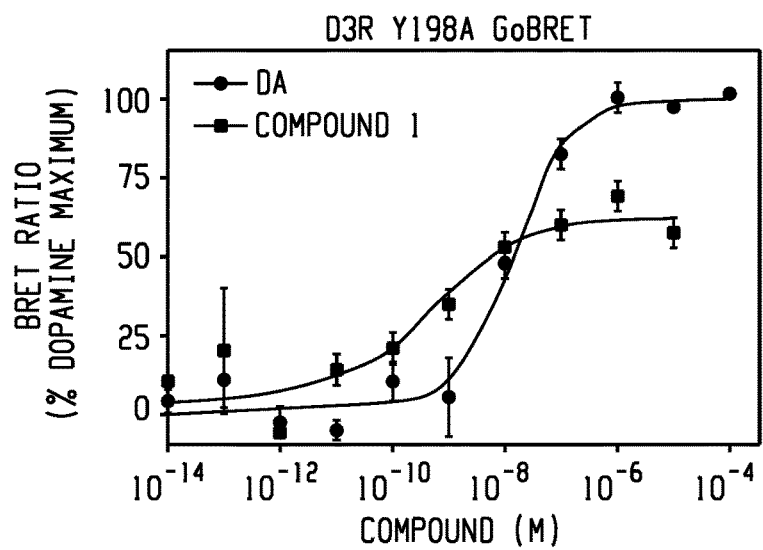
Figure 5:
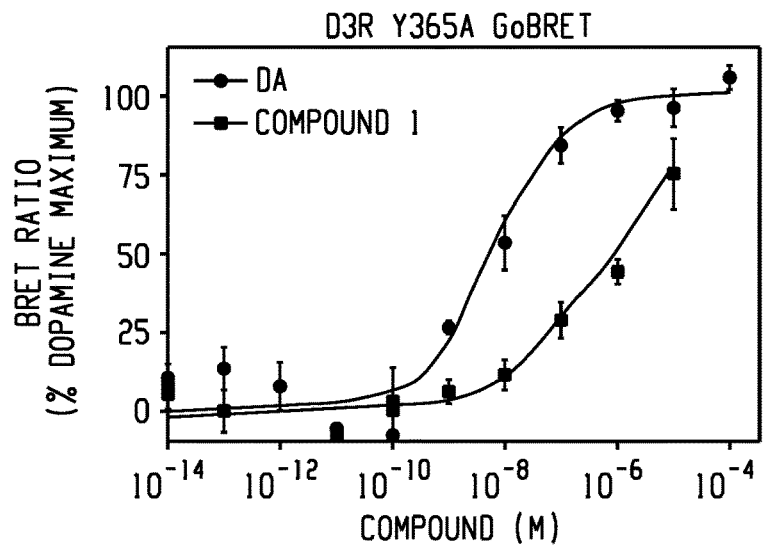

Molecular modeling studies indicated that compound 1 interacts with the D3R in a unique fashion, and identified 2 residues important for the binding of compound 1 to the D3R. Mutagenesis was conducted on these residues (Y198 and Y365) and arrestin BRET and Go BRET assays were conducted. See FIG. 5. While small effects of dopamine potency were caused by the mutants, large effects on potency and/or efficacy of compound 1 were observed. The Y198A mutation reduced the signaling efficacy of compound 1 to 36% that of dopamine in the arrestin BRET assay, and to 64% that of dopamine in the Go BRET assay, while displaying minimal effects on the potency of compound 1. The Y365A mutation had more dramatic effects. In the arrestin assay, the efficacy of compound 1 was reduced to 21% that of dopamine, and the potency of compound 1 was reduced 440-fold. In the Go BRET assay, the efficacy of compound 1 appeared to be unaffected, but the potency was reduced 25,000-fold. The results indicate compound 1 interacts with the D3R in a unique fashion compared to the endogenous agonist dopamine, which could account for its striking D3R selectivity.

Example 11. Neuroprotection Assay

Figure 6A:
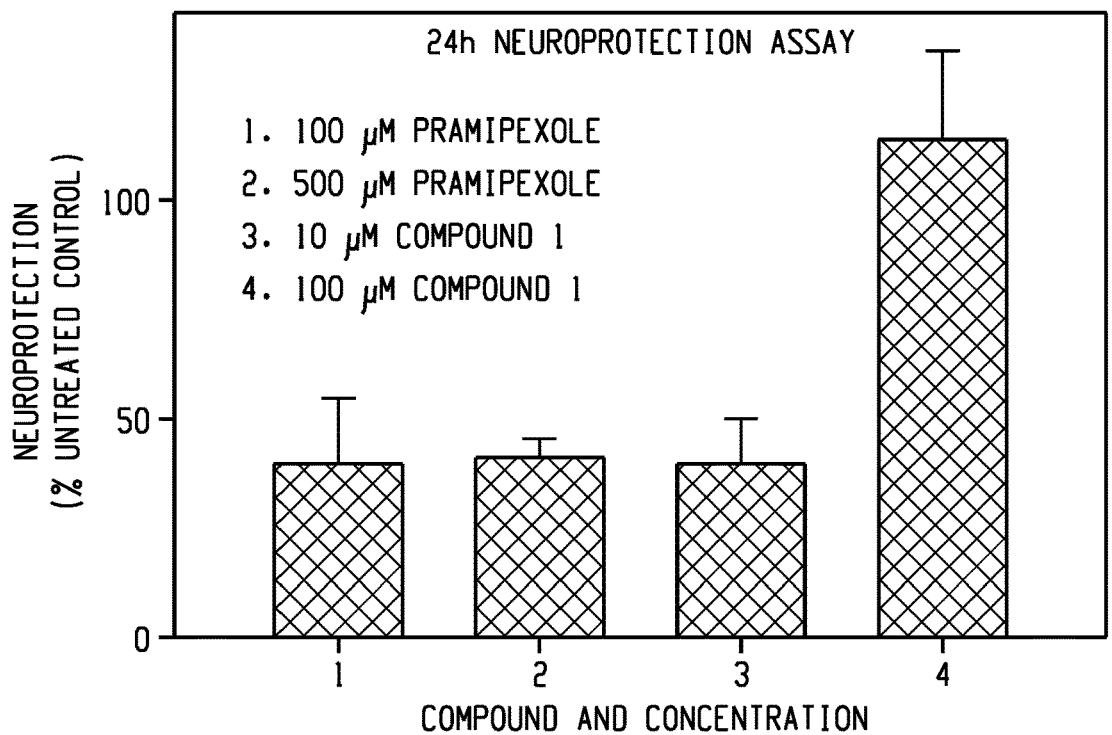
FIG. 6A. A graph of neuroprotection (% untreated control) versus compound and dose, illustrating a cell-based neuroprotection assay for Compound 1 and pramipexole as a comparator.
Figure 6B:
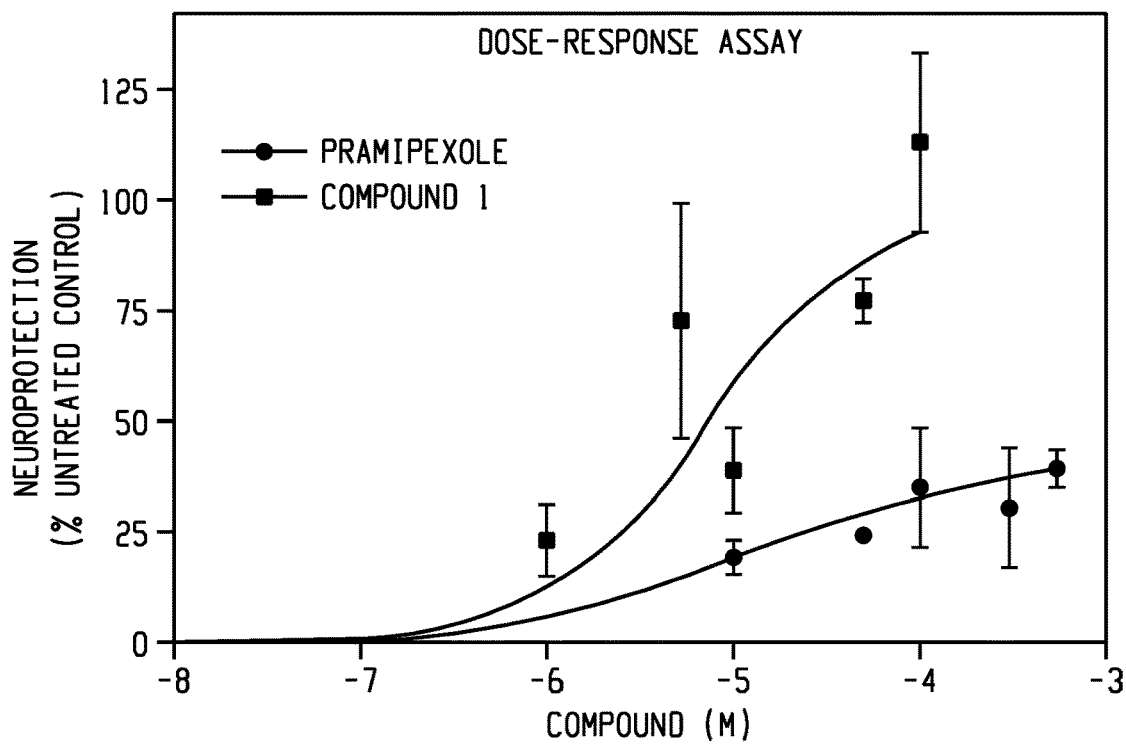
FIG. 6B. A graph of neuroprotection (% untreated control) versus concentration of Compound 1 (molar, M), illustrating a cell-based neuroprotection assay for Compound 1.

Because prior studies have found that partially selective $D_3$ DAR preferring agonists, such as pramipexole, elicit neuroprotective effects, we sought to examine the potential of a test compound of Formula I to show similar activity in a model of neurodegeneration. SHSY5Y cells were terminally differentiated for 1 week using 10 µM retinoic acid and 80 nM phorbol 12-myristate 13-acetate, after which they display a neuronal phenotype including the expression of $D_3$ dopamine receptors. Cells were pretreated with either pramipexole or Compound 1 for 24 h followed by 10 µM treatment with the neurotoxin 6-hydroxydopamine to induce neuronal insult. Protection against total neurite length decrease was measured 24 h later. For dose-response assays, terminally differentiated SHSY5Y cells were pretreated with Compound 1 for 24 h followed by 10 µM treatment with 6-hydroxydopamine, and protection against total neurite length decrease was measured 24 h later. The results are shown in FIG. 6A and FIG. 6B. As shown by FIG. 6A, Compound 1 demonstrates neuroprotection superior to pramipexole under the assay conditions. As shown by FIG. 6B, the neuroprotection provided by Compound 1 shows clear concentration dependent effect.

Example 12. Ames Testing

The mutagenicity potential of Compound 1 was tested using the Ames reverse mutation assay. Briefly, 10 million bacteria were exposed in triplicate to Compound 1 for 90 min in medium containing a low concentration of histidine. The cultures were then diluted into an indicator medium lacking histidine, dispensed into a 384-well plate, and incubated for 48 h at 37° C. Cells that have undergone a reversion will grow, resulting in a color change. The number of wells showing growth were counted and compared to the vehicle control. An increase in the number of colonies of at least 2-fold over baseline and a dose response indicated a positive response. Data were analyzed using an unpaired, one-sided Student's T-test. Where indicated, S9 fraction from the livers of Aroclor 1254-treated rats were included in the incubation at a 4.5% final concentration. An NADPH-regenerating system was also included to ensure a steady supply of reducing equivalents. The test results are shown in Table 10.

TABLE 10

| | Test Strain | S9 | AMES Result | Highest Conc. Tested | Result |
|---|---|---|---|---|---|
| Compound 1 | TA98 | No | Negative | 2,000 µg/ml | No genotoxicity observed |
| | TA100 | No | Negative | 2,000 µg/ml | |
| | TA98 | Yes | Negative | 2,000 µg/ml | |
| | TA100 | Yes | Negative | 2,000 µg/ml | |

Example 13. Cytotoxicity Screening Panel

HepG2 cells were plated on 384-well tissue culture treated black walled clear bottomed polystyrene plates. The cells were dosed with test compound at a range of concentrations. At the end of the incubation period, the cells were loaded with the relevant dye/antibody for each cell health marker. The plates were then scanned using an automated fluorescent cellular imager, ArrayScan® (Thermo Scientific Cellomics). Cytotoxicity was assessed using a multi-parametric approach using High Content Screening (HCS). The following parameters were screened.

Nuclear size: An increase in nuclear area can indicate necrosis or G2 cell cycle arrest and a decrease can indicate apoptosis.

DNA structure: An increase in DNA structure can indicate chromosomal instability and DNA fragmentation.

Cell membrane permeability: An increase in cell membrane permeability is a general indicator of cell death.

Mitochondrial mass: A decrease in mitochondrial mass indicates loss of total mitochondria and an increase implies mitochondrial swelling or an adaptive response to cellular energy demands.

Mitochondrial membrane potential ($\Delta\psi m$): A decrease indicates a loss of mitochondrial membrane potential and mitochondrial toxicity, as well as a potential role in apoptosis signaling, an increase in mitochondrial membrane potential indicates an adaptive response to cellular energy demands.

Cytochrome c: An increase in cytochrome c release is one of the hallmarks of the apoptosis cascade.

The results of the cytotoxicity screen are shown in Table 11. All cell health marker assays showed minimal cytoxicity liability of Compound 1, as the $AC_{50}$ was greater than 50 μM in each assay.

TABLE 11

| Cell Health Parameter | Response Direction | MEC (μM) | $AC_{50}$ (μM) |
|---|---|---|---|
| Nuclear Size | ↑ | 12.0 | >50 |
| DNA Structure | ↑ | 13.9 | >50 |
| Cell Membrane Permeability | ↑ | 8.58 | >50 |
| Mitochondrial Mass | ↑ | 11.9 | >50 |
| Mitochondrial Membrane Potential | ↓ | 9.28 | >50 |
| Cytochrome c | ↑ | 6.03 | >50 |

MEC is the Minimum effective concentration that significantly crosses vehicle control threshold. AC50 is the concentration at which 50% maximum effect is observed for each cell health parameter.

Example 14. Plasma and Brain Tissue Sampling

The levels of Compound 1 in mouse plasma and brain tissue samples were assessed as follows.

Figure 7A:
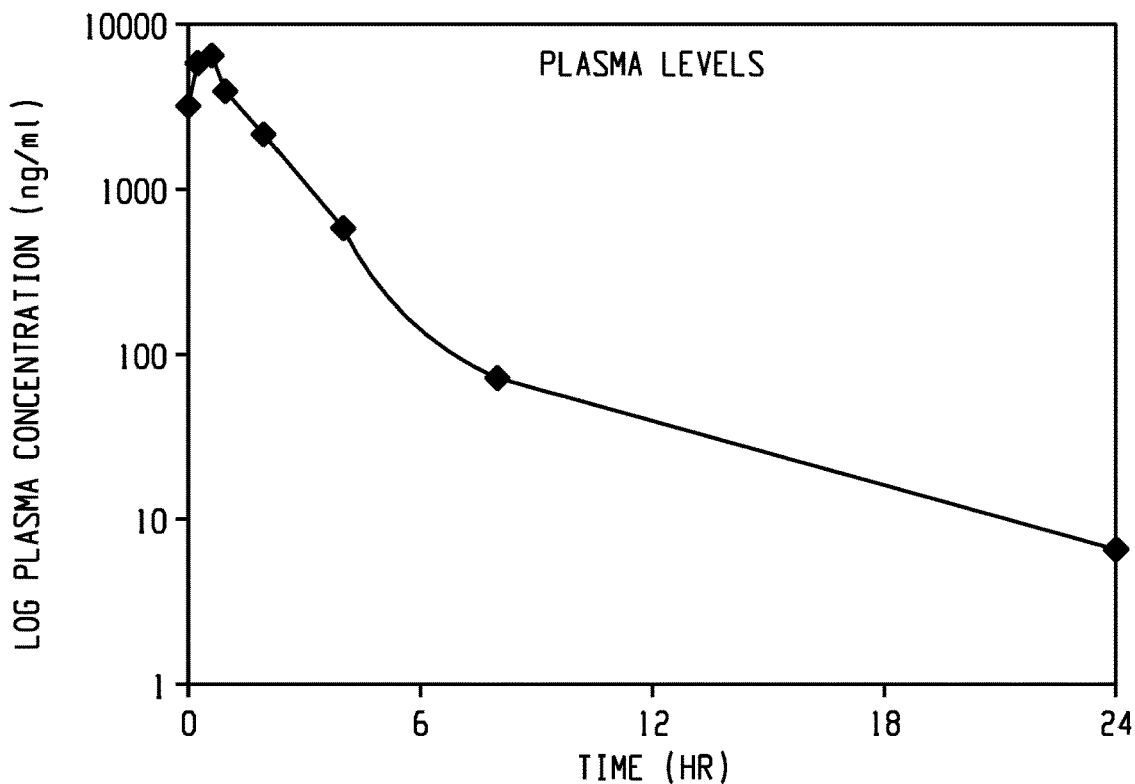
FIG. 7. Mouse Plasma level of Compound 1 as a function of time following administration of a single IP dose (20 mg/kg).
FIG. 7B Mouse Brain level of Compound 1 as a function of time following administration of a single IP dose (20 mg/kg).
Figure 7B:
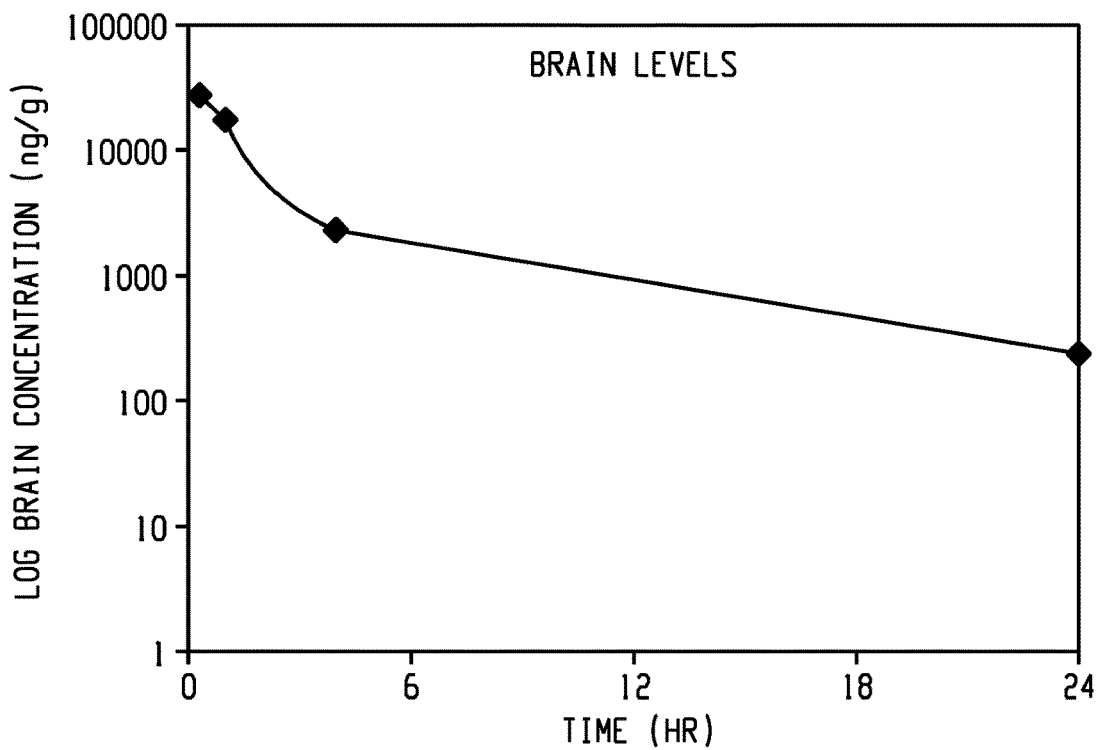

A single IP dose (20 mg/kg) of Compound 1 was administered to C57BL/6 mice. The formulation consisted of 10% dimethylacetamide (DMA) and 60% PEG400, balanced with 30% saline. Plasma and brain samples were collected across 8 time points (5, 15, 30, 60, 120, 240, 480, and 1440 minutes). Brain samples were homogenized in two volumes (1:2 w/v dilution) of phosphate buffer solution (PBS). Once homogenized, the samples were crashed with three volumes of acetonitrile containing an analytical internal standard (bucetin). Samples were then centrifuged to remove precipitated protein, and the supernatant was analyzed by LC-MS/MS. All brain samples were compared to a calibration curve prepared in mouse blank brain. Plasma samples (5, 15, 30, 60 and 120 min time points) were diluted ten-fold with blank plasma. No dilutions were made for 240, 480 and 1440 min time points plasma samples. All plasma samples were crashed with three volumes of acetonitrile containing an analytical internal standard (bucetin). Samples were then centrifuged to remove precipitated protein, and the supernatant was analyzed by LC-MS/MS. All plasma samples were compared to a calibration curve prepared in mouse blank plasma. Samples were analyzed by LC-MS/MS using Waters Xevo TQ mass spectrometer coupled with an Acquity UPLC and a CTC PAL chilled autosampler, all controlled by MassLynx software (Waters). After separation on a C18 reverse phase HPLC column (Waters Acquity HSS T3 2.1×50 mm 1.8 μM) using an acetonitrile-water gradient system, peaks were analyzed by mass spectrometry (MS) using ESI ionization in MRM mode. Compound 1 levels in plasma and brain as a function of time are shown in FIG. 7.

What is claimed is:

1. A method of treating a patient suffering from Parkinson's disease, dyskinesia, Alzheimer's disease and dementia, Huntington's disease, restless legs syndrome, bipolar disorder and depression, schizophrenia, cognitive dysfunction, alcohol addiction, nicotine addiction, cocaine addiction, methamphetamine addition, and opioid addition, the method comprising administering a therapeutically effective amount of a compound of Formula I

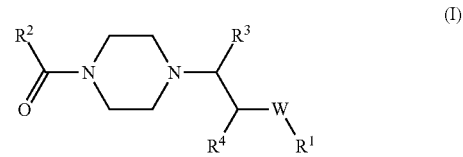

or a pharmaceutically acceptable salt thereof, wherein:
W is O or S;
$R^1$ is a phenyl; and
$R^2$ is 2-pyridyl, 3-pyridyl, 4-pyridyl, or pyrolyl group, or a 6,5-bicyclic heteroaryl group, having 1, 2, 3, 4, 5, or 6 heteroatoms independently chosen from N, O, and S, wherein the point of attachment in Formula I is in the 5-membered ring, and the 5-membered ring contains at least one heteroatom; where
$R^1$ and $R^2$ are each optionally substituted with 1 or more substituents independently chosen from halogen, hydroxyl, cyano, nitro, oxo, —$CONH_2$, amino, mono- and di-$C_1$-$C_4$alkylcarboxamide, ($C_3$-$C_6$cycloalkyl)$C_0$-$C_2$alkyl, and $C_1$-$C_6$hydrocarbyl, which $C_1$-$C_6$hydrocarbyl group is a hydrocarbon chain in which the carbon atoms are joined by single, double or triple bonds, and any one carbon atom can be replaced by O, NH, or N($C_1$-$C_4$alkyl) and which hydrocarbyl group is optionally substituted with one or more substituents independently chosen from hydroxyl, oxo, halogen, and amino; and
$R^3$ and $R^4$ are independently hydrogen or methyl.

2. The method of claim 1, wherein the compound of Formula I or a pharmaceutically acceptable salt thereof is a first active agent and is administered together with one or more additional active agents.

3. The method of claim 2, wherein one of the one or more additional active agents is L-DOPA.

4. The method of claim 1, wherein $R^3$ and $R^4$ are both hydrogen.

5. The method of claim 1, wherein the compound of Formula I is a compound of Formula I-A

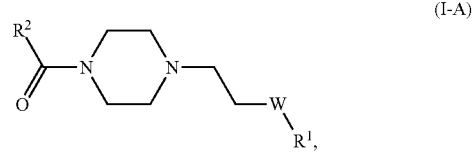

wherein:

R² is a 6,5-bicyclic heteroaryl group, having 1, 2, 3, 4, 5, or 6 heteroatoms independently chosen from N, O, and S, wherein the point of attachment in Formula I-A is in the 5-membered ring, and the 5-membered ring contains at least one heteroatom; where R² is substituted with 0 or 1 or more substituents independently chosen from halogen, hydroxyl, cyano, nitro, oxo, —CONH₂, amino, mono- and di-C₁-C₄alkylcarboxamide, (C₃-C₆cycloalkyl)C₀-C₂alkyl, and C₁-C₆hydrocarbyl, which C₁-C₆hydrocarbyl group is a hydrocarbon chain in which the carbon atoms are joined by single, double or triple bonds, and any one carbon atom can be replaced by O, NH, or N(C₁-C₄alkyl) and which hydrocarbyl group is optionally substituted with one or more substituents independently chosen from hydroxyl, oxo, halogen, and amino.

6. The method of claim 1, wherein

R² is a 6,5-bicyclic heteroaryl group selected from the following optionally substituted 6,5-bicyclic heteroaryl groups:

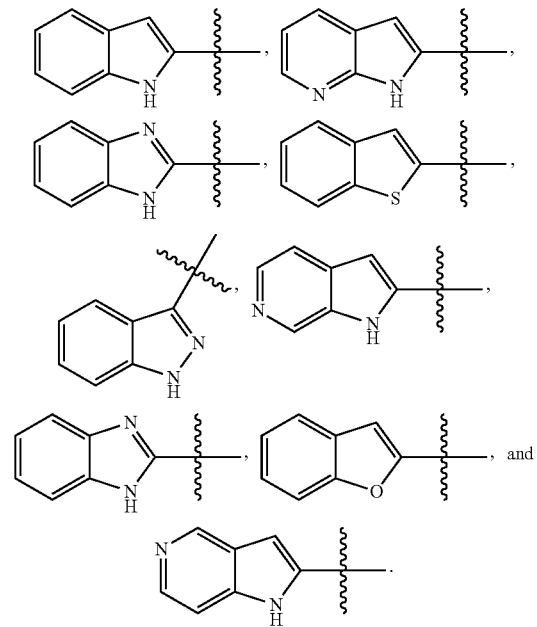

7. The method of claim 1, wherein

R² is a 2-pyridyl, 3-pyridyl, 4-pyridyl, or pyrolyl group, each of which is optionally substituted.

8. The method of claim 1, wherein R² is a 6,5-bicyclic heteroaryl group substituted with 0 or 1 or more substituents independently chosen from halogen, hydroxyl, cyano, nitro, —CONH₂, amino, C₁-C₆alkyl, C₁-C₆alkoxy, C₂-C₄alkanoyl, C₁-C₄alkylester mono- and di-C₁-C₄alkylamino, mono- and di-C₁-C₄alkylcarboxamide, (C₃-C₆cycloalkyl)C₀-C₂alkyl, and any one carbon atom in a C₁-C₆alkyl or C₁-C₆alkoxy can be replaced by O, NH, or N(C₁-C₄alkyl) and which C₁-C₆alkyl or C₁-C₆alkoxy is optionally substituted with one or more substituents independently chosen from hydroxyl, halogen, and amino.

9. The method of claim 1, wherein R² is

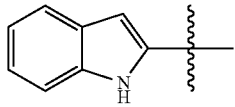 [SMILES: *c1cc2ccccc2[nH]1]

which is substituted with 0 or 1 or more substituents independently chosen from halogen, hydroxyl, cyano, nitro, —CONH₂, amino, C₁-C₆alkyl, C₁-C₆alkoxy, C₂-C₄alkanoyl, C₁-C₄alkylester mono- and di-C₁-C₄alkylamino, mono- and di-C₁-C₄alkylcarboxamide, (C₃-C₆cycloalkyl)C₀-C₂alkyl, and any one carbon atom in a C₁-C₆alkyl or C₁-C₆alkoxy can be replaced by O, NH, or N(C₁-C₄alkyl) and which C₁-C₆alkyl or C₁-C₆alkoxy is optionally substituted with one or more substituents independently chosen from hydroxyl, halogen, and amino.

10. The method of claim 1, wherein R² is a 6,5-bicyclic heteroaryl group substituted with 0 or 1 to 3 substituents independently selected from halogen, C₁-C₂alkyl, and C₁-C₂alkoxy.

11. The method of claim 1, wherein W is S.

12. The method of claim 1, wherein W is O.

13. The method of claim 1, wherein R¹ is substituted with 0 or 1 or more substituents independently chosen from halogen, hydroxyl, cyano, nitro, —CONH₂, amino, C₁-C₆alkyl, C₁-C₆alkoxy, C₂-C₄alkanoyl, C₁-C₄alkylester mono- and di-C₁-C₄alkylamino, mono- and di-C₁-C₄alkylcarboxamide, (C₃-C₆cycloalkyl)C₀-C₂alkyl, and any one carbon atom in a C₁-C₆alkyl or C₁-C₆alkoxy can be replaced by O, NH, or N(C₁-C₄alkyl) and which C₁-C₆alkyl or C₁-C₆alkoxy is optionally substituted with one or more substituents independently chosen from hydroxyl, oxo, halogen, and amino.

14. The method of claim 1, wherein R¹ is substituted with 0 or 1 to 3 substituents independently chosen from halogen, C₁-C₂alkyl, and C₁-C₂alkoxy.

15. The method of claim 1, wherein R¹ is 4-methoxyphenyl.

16. The method of claim 1, wherein the compound of Formula I is a compound in which R³ is hydrogen, R⁴ is hydrogen, -W-R¹ and R² have the following values:

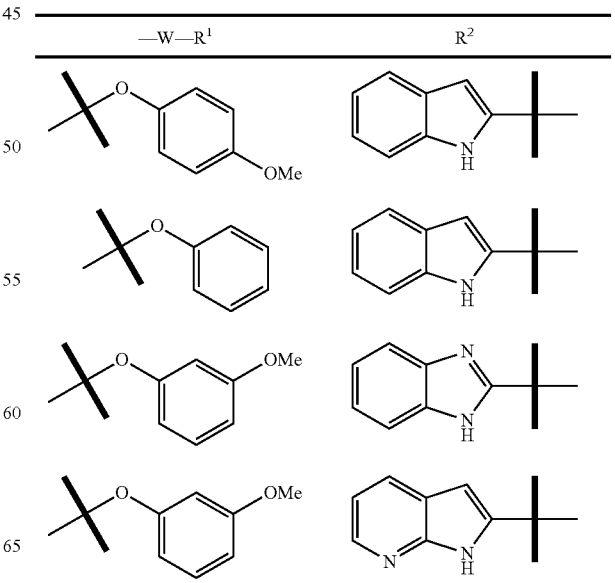

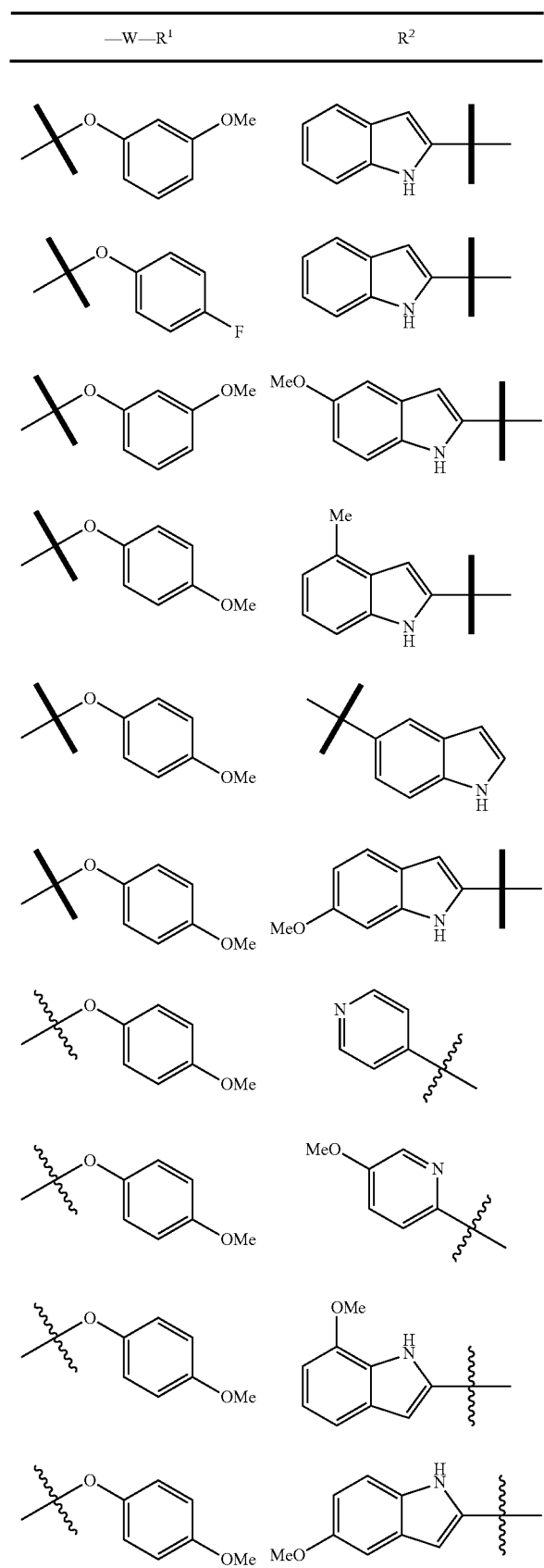

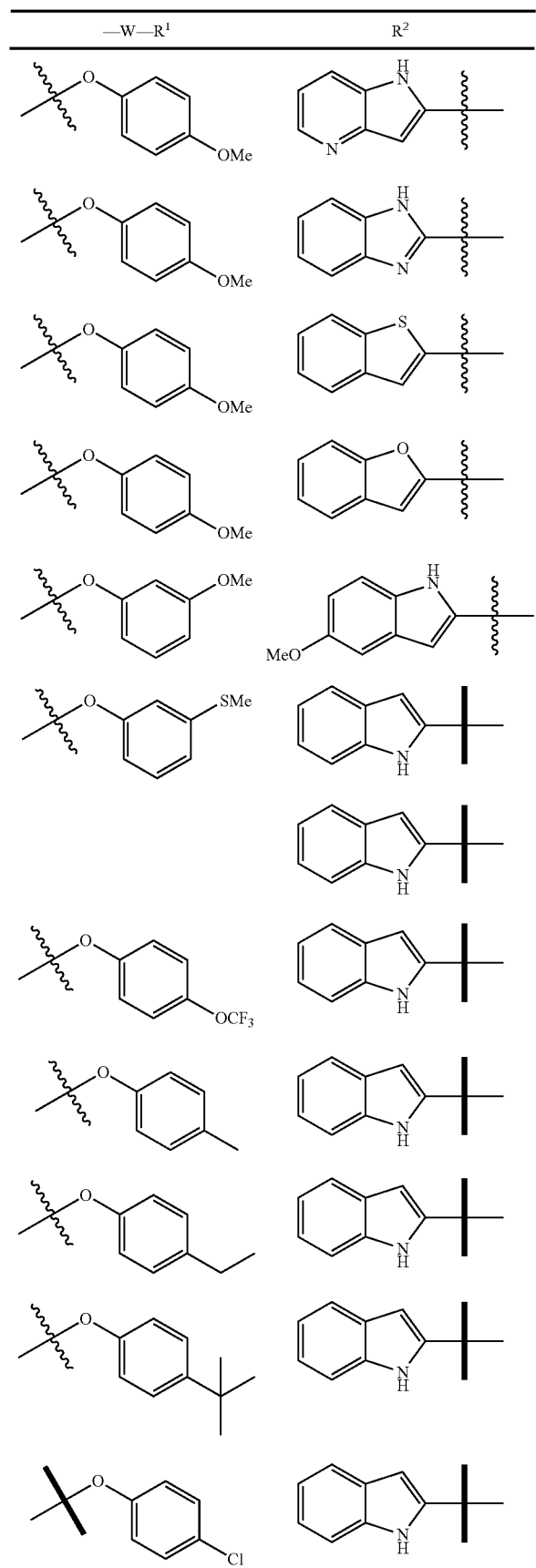

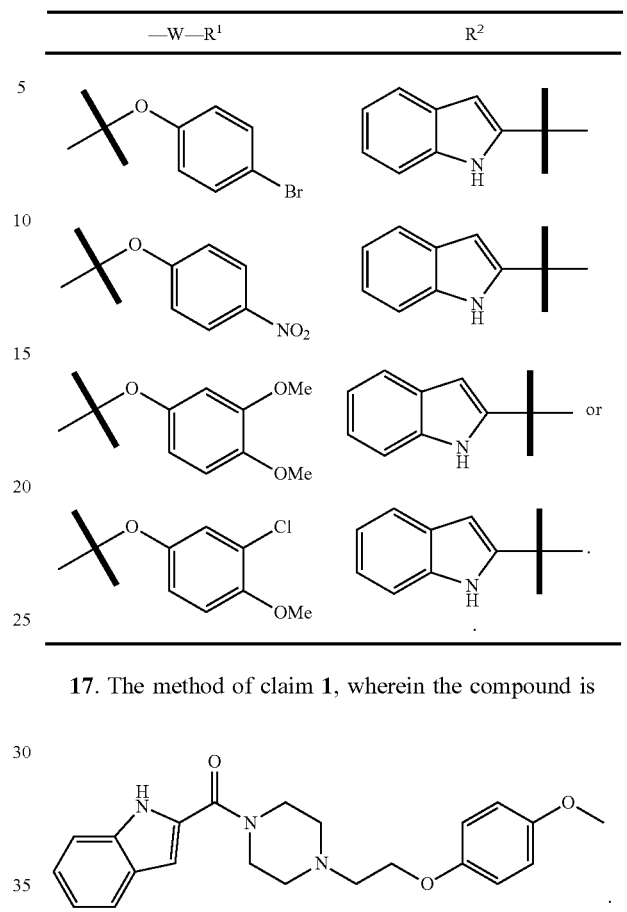

17. The method of claim 1, wherein the compound is

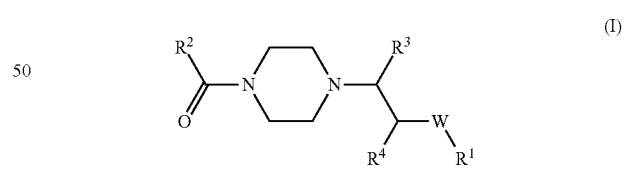

18. A method of treating a patient suffering from Parkinson's disease, dyskinesia, Alzheimer's disease and dementia, Huntington's disease, restless legs syndrome, bipolar disorder and depression, schizophrenia, cognitive dysfunction, alcohol addiction, nicotine addiction, cocaine addiction, methamphetamine addition, and opioid addition, the method comprising administering a therapeutically effective amount of a compound of Formula I (I)

or a pharmaceutically acceptable salt thereof, wherein:
W is O or S;
$R^1$ is a phenyl; and
$R^2$ is a phenyl, a 5 or 6-membered heteroaryl, having 1, 2, 3, or 4 heteroatoms independently chosen from N, O, and S or a 6,5-bicyclic heteroaryl group, having 1, 2, 3, 4, 5, or 6 heteroatoms independently chosen from N, O, and S, wherein the point of attachment in Formula I is in the 5-membered ring, and the 5-membered ring contains at least one heteroatom; where
$R^1$ and $R^2$ are each optionally substituted with 1 or more substituents independently chosen from halogen, hydroxyl, cyano, nitro, oxo, —CONH$_2$, amino, mono- and di-C$_1$-C$_4$alkylcarboxamide, (C$_3$-C$_6$cycloalkyl)C$_0$-C$_2$alkyl, and C$_1$-C$_6$hydrocarbyl, which C$_1$-C$_6$hydrocarbyl group is a hydrocarbon chain in which the carbon atoms are joined by single, double or triple bonds, and any one carbon atom can be replaced by O, NH, or N(C$_1$-C$_4$alkyl) and which hydrocarbyl group is optionally substituted with one or more substituents independently chosen from hydroxyl, oxo, halogen, and amino; and R$^3$ and R$^4$ are independently hydrogen or methyl, wherein the compound of Formula I or a pharmaceutically acceptable salt thereof is a first active agent and is administered together with one or more additional active agents; and wherein one of the one or more additional active agents is L-DOPA.

19. The method of claim 18, wherein the compound of Formula I is a compound in which R$^3$ is H, R$^4$ is H, and -W-R$^1$ and R$^2$ have the following values:

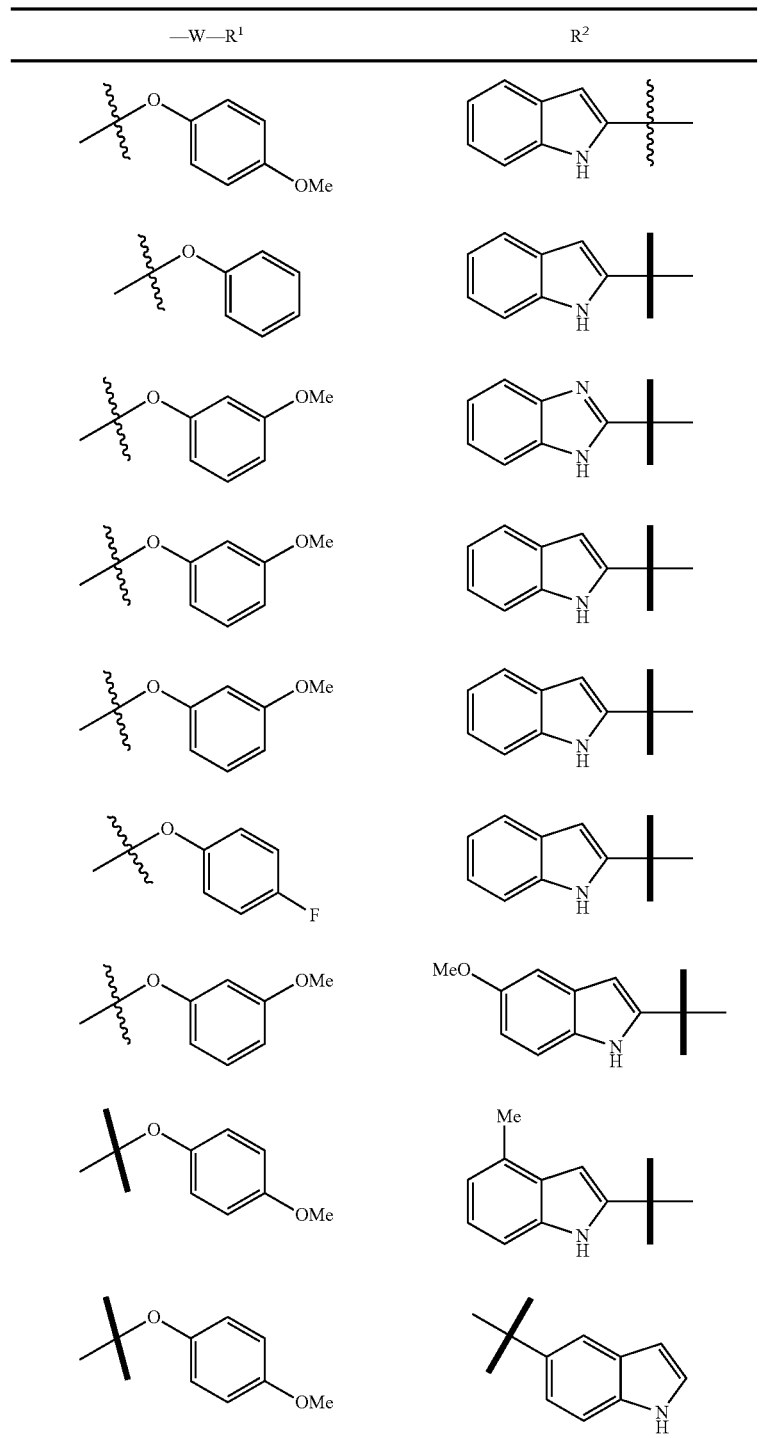

-continued
| —W—R¹ | R² |
|---|---|
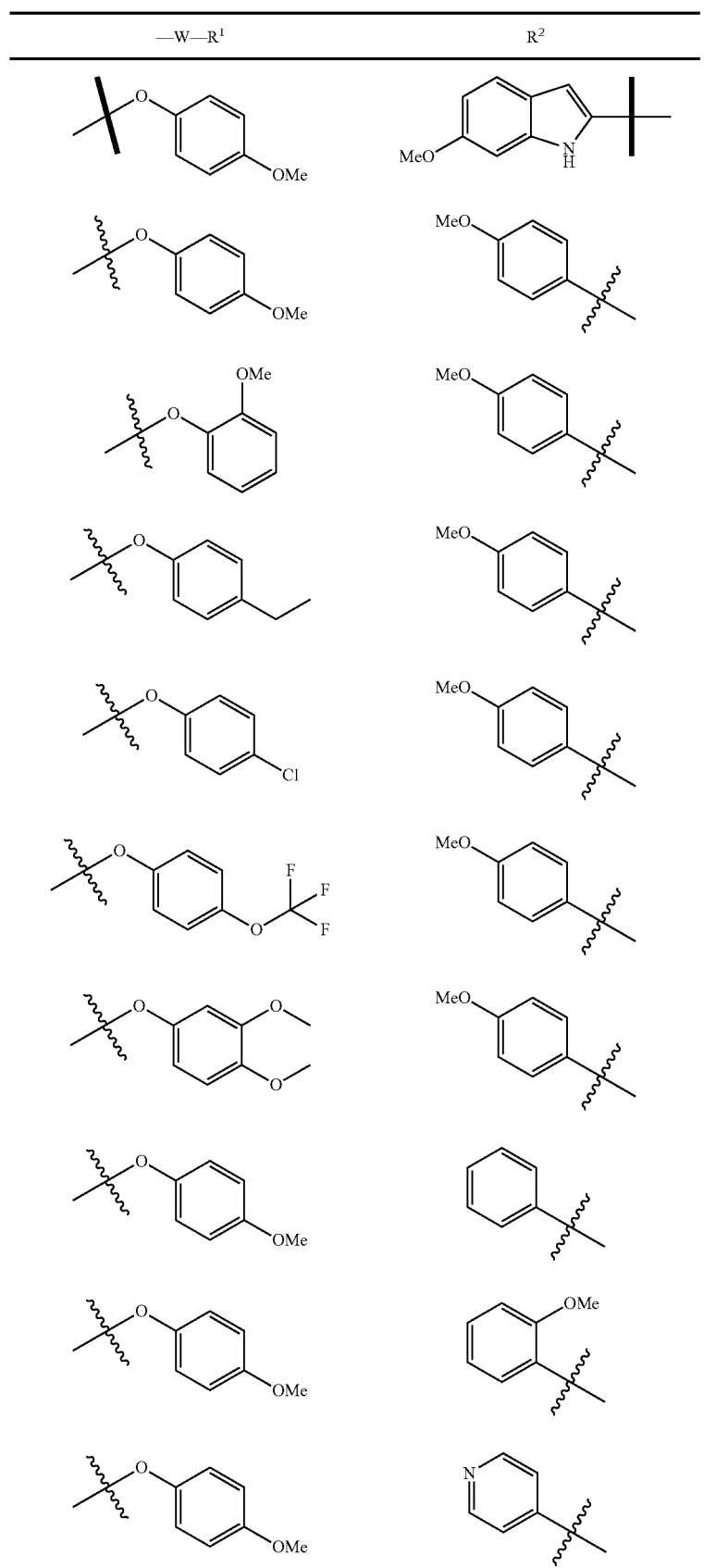

-continued
| —W—R¹ | R² |
|---|---|
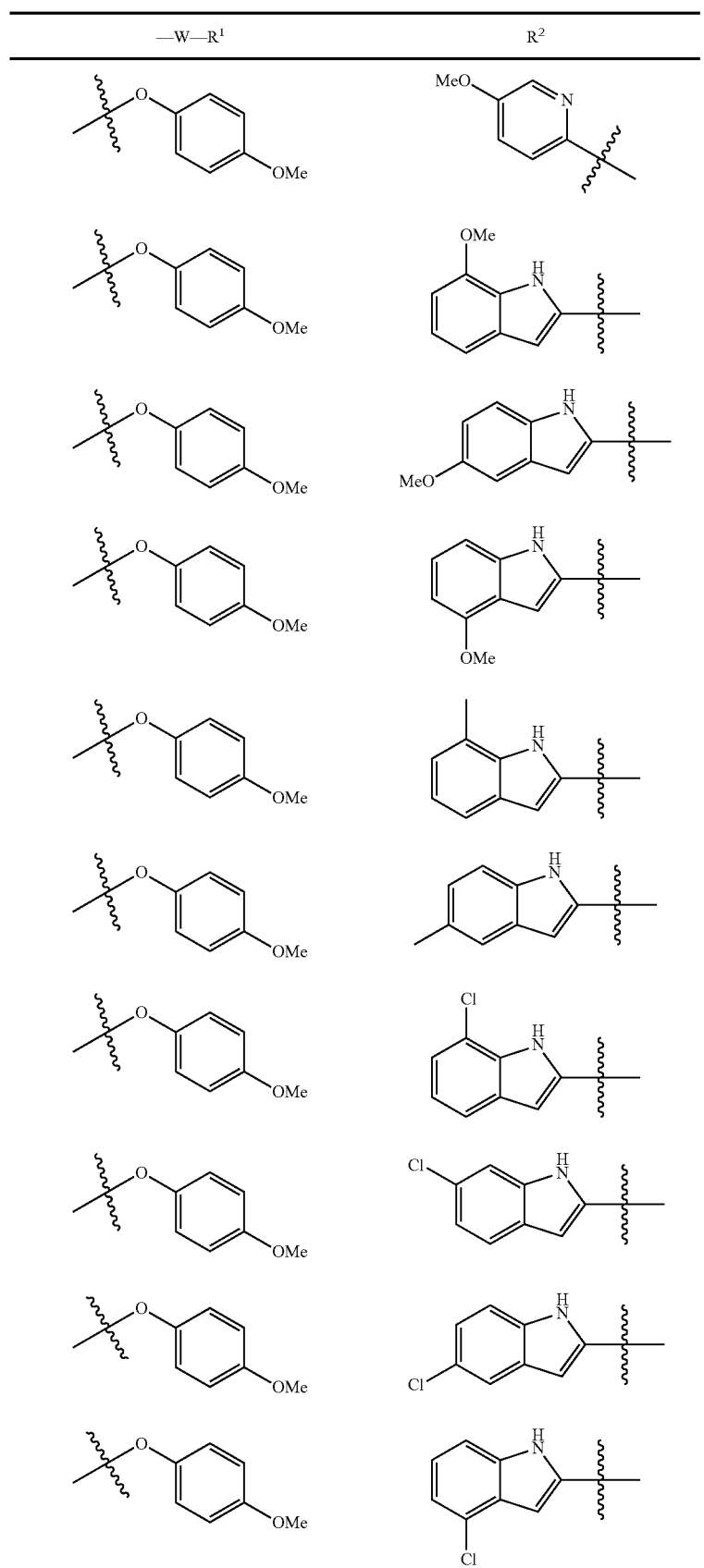

-continued
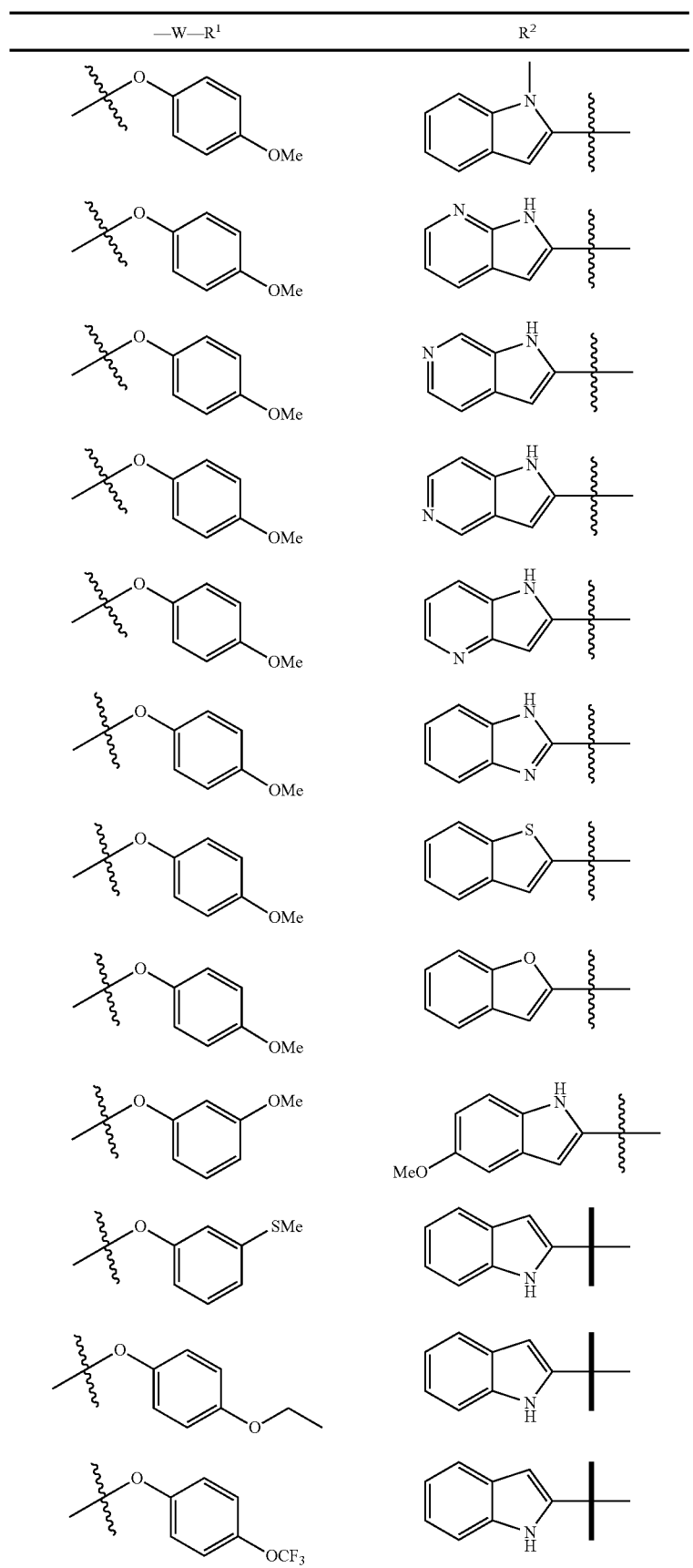

-continued

| —W—R¹ | R² |
|---|---|
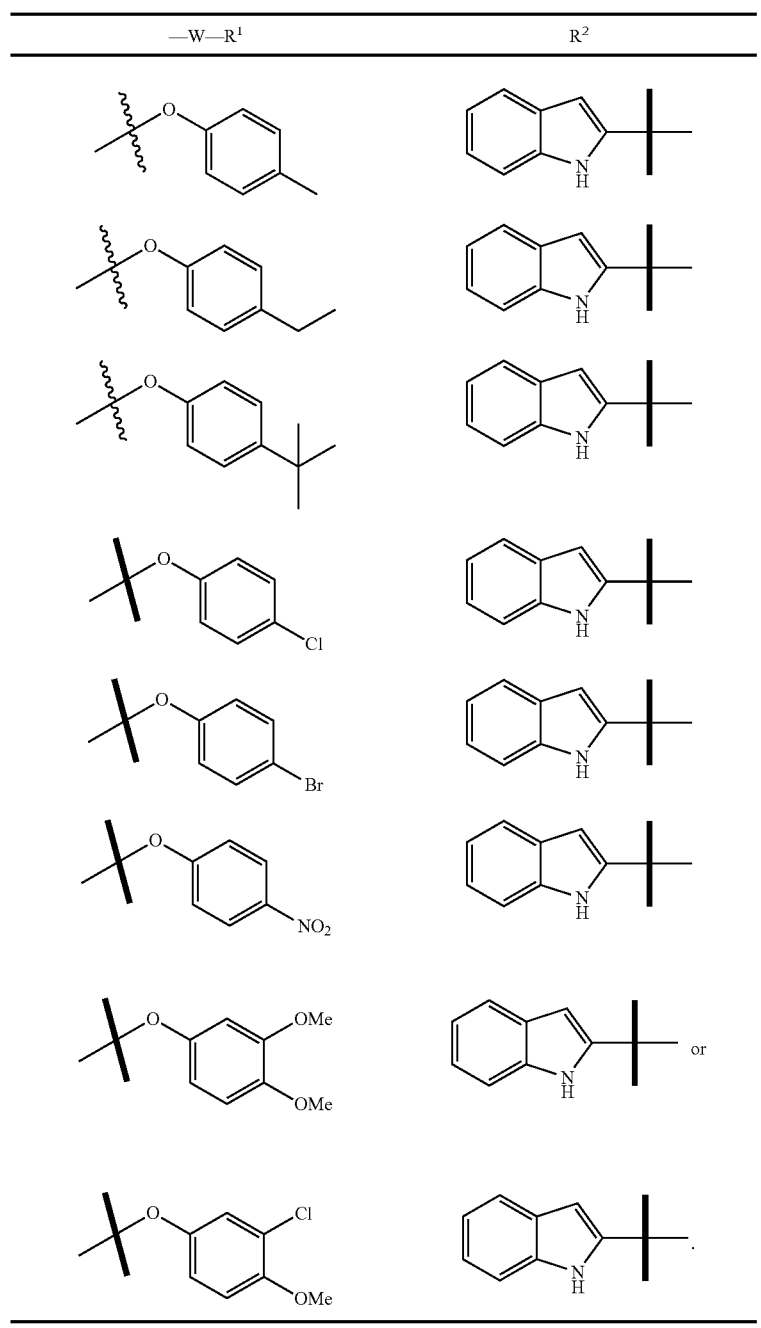

20. A method of treating a patient suffering dyskinesia secondary to treating Parkinson's disease with L-DOPA, the method comprising administering a therapeutically effective amount of a compound of Formula I

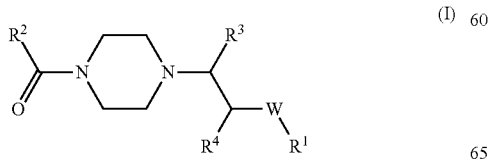

or a pharmaceutically acceptable salt thereof, wherein:
W is O or S;
R¹ is a phenyl; and
R² is a phenyl, a 5 or 6-membered heteroaryl, having 1, 2, 3, or 4 heteroatoms independently chosen from N, O, and S or a 6,5-bicyclic heteroaryl group, having 1, 2, 3, 4, 5, or 6 heteroatoms independently chosen from N, O, and S, wherein the point of attachment in Formula I is in the 5-membered ring, and the 5-membered ring contains at least one heteroatom; where
R¹ and R² are each optionally substituted with 1 or more substituents independently chosen from halogen, hydroxyl, cyano, nitro, oxo, —CONH₂, amino, mono- and di-$C_1$-$C_4$alkylcarboxamide, ($C_3$-$C_6$cycloalkyl)$C_0$-

C$_2$alkyl, and C$_1$-C$_6$hydrocarbyl, which C$_1$-C$_6$hydrocarbyl group is a hydrocarbon chain in which the carbon atoms are joined by single, double or triple bonds, and any one carbon atom can be replaced by O, NH, or N(C$_1$-C$_4$alkyl) and which hydrocarbyl group is optionally substituted with one or more substituents independently chosen from hydroxyl, oxo, halogen, and amino; and R$^3$ and R$^4$ are independently hydrogen or methyl.

21. The method of claim 20, wherein the compound is

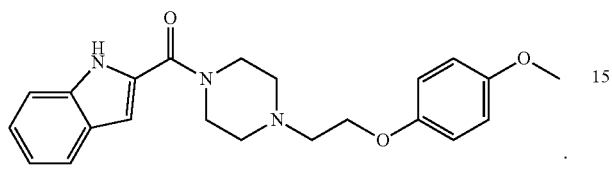

* * * * *